United States Patent
Hittinger et al.

(10) Patent No.: US 9,879,270 B2
(45) Date of Patent: Jan. 30, 2018

(54) CONSTRUCTS AND METHODS FOR GENOME EDITING AND GENETIC ENGINEERING OF FUNGI AND PROTISTS

(71) Applicant: Wisconsin Alumni Research Foundation, Madison, WI (US)

(72) Inventors: Christopher Todd Hittinger, Madison, WI (US); William Gerald Alexander, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/826,566

(22) Filed: Aug. 14, 2015

(65) Prior Publication Data
US 2016/0046952 A1 Feb. 18, 2016

Related U.S. Application Data

(60) Provisional application No. 62/037,963, filed on Aug. 15, 2014, provisional application No. 62/134,384, filed on Mar. 17, 2015.

(51) Int. Cl.
*C12Q 1/68* (2006.01)
*C12N 15/80* (2006.01)
*C12Q 1/04* (2006.01)

(52) U.S. Cl.
CPC ............ *C12N 15/80* (2013.01); *C12Q 1/045* (2013.01)

(58) Field of Classification Search
None
See application file for complete search history.

(56) References Cited

U.S. PATENT DOCUMENTS

| | | | |
|---|---|---|---|
| 2014/0068797 A1* | 3/2014 | Doudna | C12N 15/102 800/18 |
| 2016/0160224 A1* | 6/2016 | Striepen | C12N 15/79 435/471 |

OTHER PUBLICATIONS

Alexander, W. et al., "High-Efficiency Genome Editing and Allele Replacement in Prototrophic and Wild Strains of *Saccharomyces*," (2014) Genetics 198:859-866.

Dicarlo, J. et al., "Genome Engineering in *Saccharomyces cerevisiae* Using CRISPR-Cas Systems," (2013) Nucleic Acids Research 41(7):4336-4343.

Gaj, T. et al., "ZFN, TALEN, and CRISPR/Cas-Based Methods for Genome Engineering," (2013) Trends in Biotechnology 31(7):397-405.

"The CRISPR Craze," (2013) Science 341:833-836.

Storici, F. et al., "In Vivo Site-Directed Mutagenesis Using Oligonucleotides," (2001) Nature Biotechnology 19 (8):773-776.

Stuckey, S. et al., "Gene Knockouts, in Vivo Site-Directed Mutagenesis and Other Modifications Using the Delitto Perfetto System in *Saccharomyces cerevisiae*" (2011) Methods in Enzymology 533:103-131.

* cited by examiner

*Primary Examiner* — Jim Ketter
(74) *Attorney, Agent, or Firm* — Andrus Intellectual Property Law, LLP

(57) ABSTRACT

Provided herein are constructs for genome editing or genetic engineering in fungi or protists, methods of using the constructs and media for use in selecting cells. The construct include a polynucleotide encoding a thymidine kinase operably connected to a promoter, suitably a constitutive promoter; a polynucleotide encoding an endonuclease operably connected to an inducible promoter; and a recognition site for the endonuclease. The constructs may also include selectable markers for use in selecting recombinations.

20 Claims, 8 Drawing Sheets

Fig. 5A
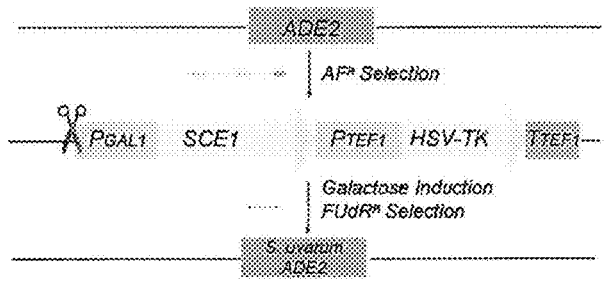
Fig. 5B
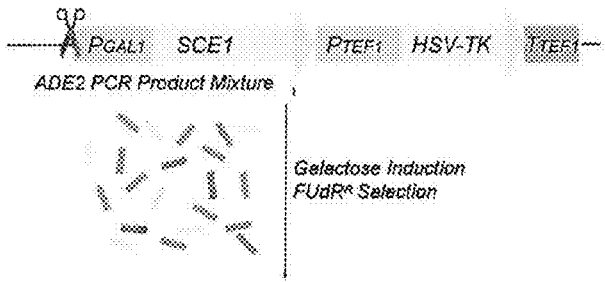
Fig. 5C
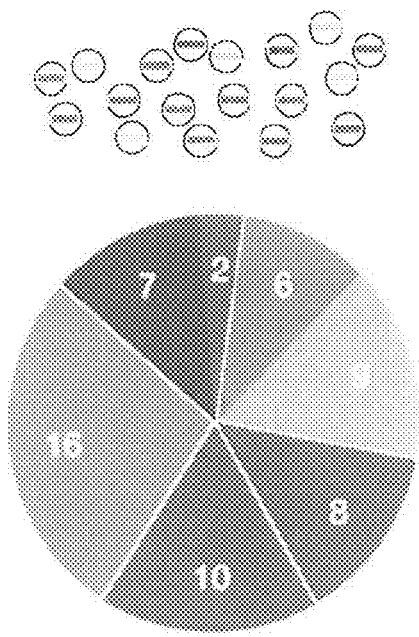
Fig. 5D
Figure 5

CONSTRUCTS AND METHODS FOR GENOME EDITING AND GENETIC ENGINEERING OF FUNGI AND PROTISTS

CROSS-REFERENCE TO RELATED APPLICATIONS

This patent application claims the benefit of priority of U.S. Provisional Patent Application No. 62/037,963, filed Aug. 15, 2014 and of U.S. Provisional Patent Application No. 62/134,384, filed Mar. 17, 2015, both of which are incorporated herein by reference in their entireties.

STATEMENT REGARDING FEDERALLY SPONSORED RESEARCH

This invention was made with government support under grant number 1253634 awarded by the National Science Foundation and grant number DE-FC02-07ER64494 awarded by the US Department of Energy. The United States government has certain rights in the invention.

SEQUENCE LISTING

This application is being filed electronically via EFS-Web and includes an electronically submitted Sequence Listing in .txt format. The .txt file contains a sequence listing entitled "2015-08-14_5671-0062_ST25.txt" created on Aug. 14, 2015 and is 84,143 bytes in size. The Sequence Listing contained in this .txt file is part of the specification and is hereby incorporated by reference herein in its entirety.

INTRODUCTION

Genome editing is a precise and powerful tool to investigate basic genetic processes or to reprogram an organism's metabolism. Techniques to precisely manipulate genomes exist for many model organisms (1-4), but not all features of these approaches are easily portable to closely related species, The genus *Saccharomyces* is highly experimentally tractable, and laboratory strains of all seven natural species can be genetically manipulated (5-7). *Saccharomyces cerevisiae* is undoubtedly the most well-known member of the genus due to its role in brewing (8), biofuels (9, 10), winemaking (11), and baking, as well as a model system for the biological sciences (12). Other members of the genus are also used by humans in the form of interspecies hybrids, such as the *S. cerevisiae*×*Saccharomyces kudriavzevii* hybrids used to ferment some wines and Belgian beers (11) and the *S. cerevisiae*×*Saccharomyces eubayanus* (6) hybrids found in the brewing of lager-style beers around the world. The *Saccharomyces* genus is also an emerging "model genus" for molecular evolution, and several experimentally tractable species are now used routinely in evolutionary genetics research (13). Efficient genome editing of these diverse *Saccharomyces* yeasts would therefore provide new avenues of investigation for basic and applied research.

One major reason for the popularity of *S. cerevisiae* as a model system is the availability of powerful genetic manipulation tools. One of these tools is the URA3 selection/counterselection system (14). URA3 is an endogenous gene required for the de novo synthesis of uracil; however, the URA3 gene can be used as a selectable marker in ura3 strains by selecting for the ability to grow on synthetic media without uracil. The deactivation or replacement of URA3 can also be selected for using synthetic media containing 5-fluoroorotic acid (FOA), as URA3 cells convert FOA into the toxic compound 5-fluorouracil, while ura3 cells are unable to convert FOA. This counterselection property of the URA3 gene allows an investigator to insert the URA3 marker anywhere in the *S. cerevisiae* genome and then seamlessly replace it with mutant or heterologous DNA of interest.

These "Insert-then-replace" engineering methods can be further enhanced by coupling a double-strand break (DSB) generator to the marker. DSBs are known to enhance homologous recombination in their immediate vicinity on the chromosome in a variety of organisms (15, 16), and, when paired with the counterselection capability of URA3, an investigator is able to recover modified strains at very high efficiencies (17-19). Unfortunately, wild and industrial strains are almost always prototrophic, preventing the use of URA3 without prior genetic manipulations. Since the impact of ura3 on growth is not fully relieved by uracil supplementation, auxotrophic strains can be more difficult to propagate and manipulate. Conclusions reached with prototrophic strains can also be more biologically relevant (20, 21), and most industrial applications require robust prototrophic strains. Thus there is a need for an improved genome editing system for yeast.

SUMMARY

Constructs, media and methods of genome editing and genetic engineering of fungi or protists are provided herein. In particular, constructs for genome editing or genetic engineering in fungi and protists are provided herein. The constructs include a first polynucleotide encoding a thymidine kinase operably connected to a first promoter, a second polynucleotide encoding an endonuclease operably connected to a second inducible promoter, and a recognition site for the endonuclease. Suitably the constructs are part of a vector that can be replicated in a host cell, such as *E. coli*. Alternatively, the constructs may be products of a PCR reaction and may include selectable markers and/or regions of at least 20 nucleotides identical to a genetic locus to allow for homologous recombination with the fungal genome.

Methods of genome editing, allele replacement or genetic engineering of a fungus or protists are also provided. The methods include generating or obtaining the construct described above and incorporating the construct into the fungal or protist cells. Once incorporated the cells are selected for thymidine kinase by growing the fungus or protist on antifolate containing medium. The methods may further include inducing the fungal or protists cells to produce the endonuclease and counter-selecting the cells in the presence of an agent that becomes toxic in the presence of thymidine kinase. The cells may also be further selected for the loss of thymidine kinase by selection on synthetic medium containing antiviral drugs such as 5-fluorodeoxyuridine (FUdR).

In another aspect, constructs including a first promoter operably connected to a first polynucleotide encoding a thymidine kinase, a second promoter operably connected to a second polynucleotide encoding a 5' portion of a first selectable marker, a third promoter operably connected to a third polynucleotide encoding a second selectable marker and a fourth polynucleotide encoding a 3' portion of the first selectable marker are provided. The second polynucleotide and the fourth polynucleotide encoding the 5' portion and the 3' portion of the first selectable marker contain a region of overlapping sequence to allow for recombination between the 5' portion and the 3' portion of the polynucleotide sequence encoding the first selectable marker.

In still another aspect, these constructs can be used in further methods of genome editing, allele replacement or genetic engineering of a fungus or protists. The constructs described herein may be introduced into a fungal or protist cell and then integration into the genome of the cell can be selected for the selecting for thymidine kinase as described above and selecting for expression of the second selectable marker, i.e. by growing the cells in media comprising an antibiotic or other agent to which the cells are susceptible and will not grow in the absence of the selectable marker but to which the selectable marker confers resistance and allows growth of the cells in the presence of the antibiotic or other agent. The selection step allows isolation of engineered fungal or protist cells incorporating at least a portion of the construct comprising at least the polynucleotide encoding the thymidine kinase at the second selectable marker onto at least one chromosome or allele. The methods may further comprise selecting the engineered fungal or protist cells for the first selectable marker and the second selectable marker to allow selection and isolation of engineered fungal or protist cells comprising at least a portion of the construct integrated into both alleles.

Finally, media for use in the methods are provided. The media include a non-fermentable carbon source such as glycerol and an antifolate such, as sulfanilamide and/or methotrexate.

BRIEF DESCRIPTION OF THE DRAWINGS

FIG. 4A is a schematic showing that the engineered S. kudriavzevii HO locus is flanked by direct repeats (arrows). hoΔ::TkMX deletion by homologous recombination will be selected for when placed under counterselective pressure. FIG. 4B is a set of photographs showing that when S. kudriavzevii hoΔ::TkMX is plated onto SC+FUdR plates, resulting FUdR$^R$ colonies cars be recovered that have removed the entire hoΔ::TkMX locus. FIG. 4C is a graph showing the average S. cerevisiae growth characteristics evaluated in YPD using a TECAN robotic plate reader. Both wild-type and restored ADE2 strains grew identically, validating the utility of TK for insert-then-replace engineering strategies, while tire ade2Δ::TkMX-URA3 strain exhibited a lower growth rate and final cell density.

FIG. 5 is a set of figures showing that HERP cassettes enable highly efficient gene replacement strategies. FIG. 5A shows that TkMX was fused to the SCEI gene driven by the galactose-inducible promoter of GAL1. FIG. 5B shows a test case where HERP1.0 was used to delete ADE2, which was in turn replaced with the ADE2 sequence from S. uvarum at a rate approaching 1% of surviving cells. FIG. 5C shows that the ade2Δ::HERP1.0 strain was transformed with a PCR product mixture containing equimolar ADE2 sequences from the seven Saccharomyces species to test the ability to recover all species from a mixture of PCR products. FIG. 5D shows that all seven species of ADE2 sequence present in the transformation reaction were observed integrated into the ADE2 locus by replacement of the HERP1.0 cassette. The proportion of the recovered strains deviated modestly from the expected proportions ($\chi^2=13.1$, $d_f=6$, P=0.03997).

DETAILED DESCRIPTION

Figure 1:
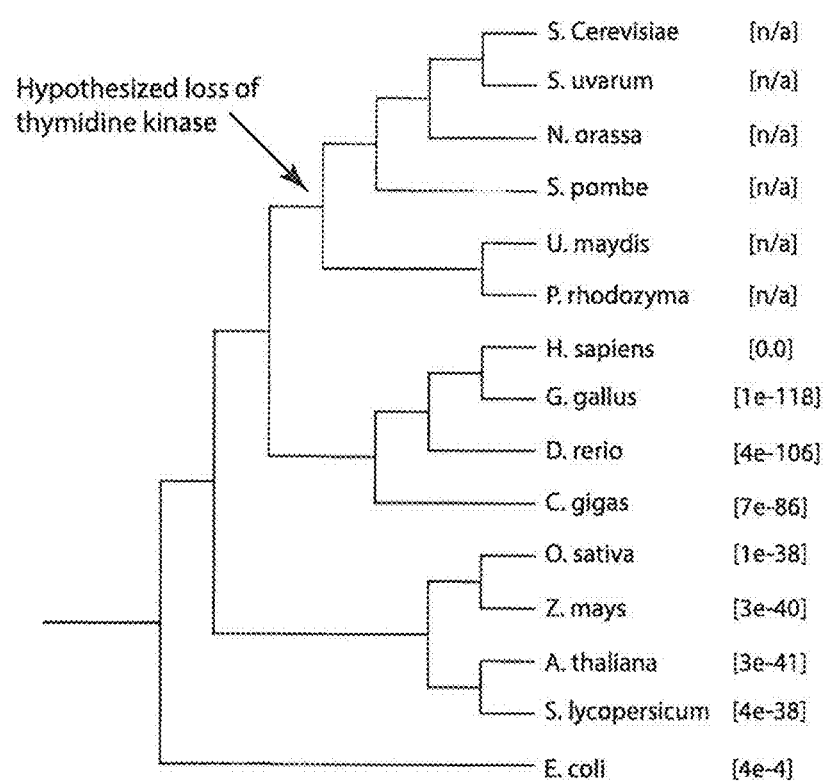
FIG. 1 is a cladogram showing that thymidine kinase was lost early in the fungal lineage. No sequenced genomes contain thymidine kinase, nor has any biochemical assay demonstrated thymidine kinase biochemical activity from fungi (gray). The lineages that retained thymidine kinase (black) include most plants, animals, and bacteria. Bracket numbers are E-values for the highest scoring sequence attributed to that species when blastp (11) using the soluble human thymidine kinase protein (GenBank: BAG70082.1) was performed with default settings. The cladogram was drawn using Geneious (12).

Efficient genome editing and engineering requires targeted double-strand breaks and marker genes that are both selectable and counter-selectable. Constructs and methods of using the constructs are provided herein that allow for the use of the gene encoding thymidine kinase (TK) from human Herpes Simplex Virus as both a selectable and counter-selectable marker in a variety of fungal species, including Saccharomyces cerevisiae, Saccharomyces mikatae, Saccharomyces kudriavzevii, Saccharomyces uvarum, and Neurospora crassa and protists species, including Trypanosoma and Euglena. Since TK is absent in all known fungi, the marker is likely of pan-fungal utility. Many protists also lack a functional thymidine kinase and the system described herein would be expected to function in these protists as well. For reliable use in genome-editing applications, media recipes and protocols had to be substantially altered to address changes in the availability of drugs and problems with thymidine transport and petite formation (loss of mitochondria) in the *Saccharomyces* genus. The thymidine kinase marker was further combined into a single cassette with a galactose-inducible meganuclease ($P_{GAL1}$-SCEI) to create a construct called HERP1.0 (Haploid Engineering Replacement Protocol).

Selectable markers were also added to HERP 1.0 as described in the Examples to generate HERP1.1 and HERP1.2. HERP1.1 and HERP1.2 are identical, except that the TK coding sequence was fused to commonly used dominant markers encoding resistance to hygromycin (HYG) and G418 (KAN), respectively. The generation of these constructs is described in the Examples section. Those of skill in the art will appreciate that various modifications as described more rally below can be made to adapt these constructs for use with other nucleases or selectable markers or in combination with marker genes.

We have demonstrated that each cassette can be amplified with long (60-90 bp) PCR primers that 1) amplify the cassette, 2) encode an I-SceI meganuclease cut site, and 3) act as crossover sites for homologous recombination to replace a specific targeted portion of the genome with the cassette. Once a cassette is inserted, a double-strand break can be induced at the site by growing the cells on galactose. Doing so dramatically increases the efficiency of transformation such that hundreds of thousands of independent transformants can be obtained in a single experiment. This high efficiency allows for high-throughput replacement of the target locus with alleles or genes (for example from across a phylogeny as shown, in the Examples), synthetic genes, or mutagenized genes. When HERP1.1 and HERP1.2 are heterozygous at a given locus, we have even shown that diploids with both alleles replaced with the desired sequence can be recovered with appreciable frequency. The ability to manipulate prototrophic and diploid strains is critical for applications in the brewing and biofuel industry where haploid and auxotrophic strains are seldom used. These new tools enable 1) efficient and direct modification of the industrial organism of choice, and 2) high-throughput screens in the relevant genetic background and industrial condition.

In addition to precise genome editing or replacement of coding sequences (singly or in designed, natural, or random pools), several other uses for the HERP cassettes can be envisioned: including but not limited to targeted or combinatorial induction of rearrangements in chromosomes, precise epitope-tagging or fusion-protein construction, precise replacement of cis-regulatory or non-coding sequences (singly or in designed, natural or random pools), combinatorial introduction of libraries of genes or pathways via homologous recombination across the double-strand break, or scarless deletion of genetic material.

Using the system described herein and as shown in the Examples, transformation rates approaching 1% of viable cells can be achieved. One application of this high gene-replacement rate is the creation of populations of cells that differ at one locus chosen by the investigator. For example, one small sample of cells could be transformed with hundreds or thousands of different PCR products, such as a library of alleles from a diverse group of organisms or synthesized DNA such as random mutations or genetically engineered DNA. The resulting pool could then be subjected to a selection regime designed to allow the growth of the sequences best fit to that condition; the most fit sequences would become over represented, while the least fit sequences would become less abundant. When mutagenic PCR or methods of synthesizing variable DNA sequences are used, pooled replacement could be used to saturate a genomic region of interest with novel mutations in a similar manner to deep mutational scanning (39). If an investigator requires more detailed phenotypic analysis, such as to evaluate biochemical or biofuel yield, a robotic colony picker could be used to isolate a subset of the hundreds of thousands of transformants generated by pooled replacement for further downstream experiments.

Another exciting application of the HERP cassettes is homozygous double replacement in diploid cells, which enables facile genome editing in industrially important diploid *Saccharomyces* strains and species for the first time. While the mechanism behind double replacement is still being investigated, we hypothesize that the high rate of gene conversion observed in *Saccharomyces* is a major factor. When HERP cassettes are present at the same locus on both chromosomes, induction and transformation would result in one of the two cassettes being replaced with the exogenous PCR product by the cell during DSB repair. Since the other locus would still have a DSB lesion, the cell will most likely repair that chromosome with the newly transformed homologous chromosome. The end result would be a diploid cell that has had both HERP cassettes replaced by DNA derived from a single PCR product. Using this surprisingly efficient approach, we expect that almost every diploid industrial and wild strain of *Saccharomyces* can now be engineered directly without creating auxotrophic strains prior to genome editing.

In the Examples and the HERP constructs provided herein the HSV-TK was driven with the MX cassette. The MX cassette includes promoter and terminator elements of the *Ashbya gossyppii* EF-1α gene. This cassette is commonly used to drive expression of genes in *Saccharomyces*. The MX cassette may be replaced in the HERP constructs with another promoter or promoter cassette including but not limited to THD3 or trpC from *Aspergillus*. In the Examples the GAL1 promoter was used to provide inducible expression of the endonuclease. Replacing the GAL1 promoter with a completely heterologous induction method, such as tetracycline-inducible systems (50) or the beta-estradiol system (McIsaac et al. Mol Biol Cell (2011) 22:4447-4459), would allow the HERP cassettes to be ported to non-Saccharomycataceae yeasts or even to filamentous fungi. Many promoter cassettes, including inducible and repressive promoter cassettes have been developed for use in yeast including but not limited to ADH2, PHO5, PGK1, GAP1, TP11, MFA1, CUP1 and MFα1. A transient or plasmid-based extrachromosomal CRISPR/Cas9 system could also fulfill the need for a universal DSB generator, allowing the HERP cassettes to provide a wide variety of fungal or protist systems with, a highly efficient and specific method for genome engineering.

The endonuclease used in the Examples was I-SceI, but other endonucleases or megaendonucleases may also be used in the constructs and methods described herein. Endonucleases such as I-SceI, I-Cre-I, I-CeuI or designer nucleases such as zinc-finger nuclease (ZFN) or transcription-activator-like effector nucleases (TALEN) have been used in cells to delete transgenes with efficiencies reaching up to 34% (Petolino et al., 2010; Weinthal et al, 2013). The I-SceI nuclease recognizes an 18 bp site and leaves a four base overhang shown by the arrows in the recognition site below:

(SEQ ID NO: 1)
5'...TAGGGATAA↓CAGGGTAAT...3'

(SEQ ID NO: 2)
3'...ATCCC↑TATTGTCCCATTA...5'.

The I-CreI nuclease recognizes a 22 bp site and leaves a four base overhang shown by the arrows in the recognition site below:

(SEQ ID NO: 3)
5'...CAAAACGTC GTGA↓GACAGTTTG...3'

(SEQ ID NO 4)
3'...GTTTTGCAG↑CACT CTGTCAAAC...5'.

The I-CeuI nuclease recognizes a 27 bp site and leaves a four base overhang shown by the arrows in the recognition site below:

(SEQ ID NO: 5 and SEQ ID NO: 6, respectively).

5'...TAACTATAACGGTCCTA▼AGGTAGCGAA...3'
3'...ATTGATATTGCCAGGATTCCATCGCTT...5'
                    ▲

Other rare cutting endonucleases are available to those of skill in the art including but not limited to I-MsoI, I-DmoI, I-SceII-VII, I-ChuI and many others.

In the Examples, the selectable markers used to generate HERP1.1 and HERP 1.2 conferred resistance to kanamycin or hygromycin. Other selectable markers conferring resistance to other antibiotics such as NAT, Sh ble or ble, which confer resistance to nourseothricin, Zeocin and phleomycin, respectively could also be used. Those of skill in the art will appreciate that additional combinations of selectable markers can be used as well.

The compositions provided herein include constructs which may include vectors, plasmids, expression cassettes or PCR amplicons which include at least a polynucleotide encoding a thymidine kinase operably connected to a promoter, a polynucleotide encoding an endonuclease operably connected to an inducible promoter and a recognition site for the endonuclease as described herein. Constructs include single-stranded RNA, double-stranded RNA, single-stranded DNA, double-stranded DNA segments, antisense RNA, PCR amplicons, or combinations thereof.

The constructs described herein may further comprise a segment of nucleotides homologous to the target fungal genome in the gene of interest or targeted site for homologous recombination. Suitably, the segment of homology is greater than 20, 30, 40, 50 or 60 nucleotides in length. The segment of homology or identical nucleotide sequence may be between 40 and 2000 nucleotides long or even longer, but may be as little as 20, 30, 40, 50, 60, 70, 80, 90, or 100 nucleotides in length. In other fungi, longer regions of sequence identity are needed for efficient homologous recombination. For example, in N. crassa at least 1000 bp of sequence overlap are generally needed. Thus the segment of identical nucleotides in the construct can be varied by those of skill in the art to balance efficient and targeted homologous recombination with the total size of the construct. The constructs may also include one or more heterologous or target polynucleotide for insertion and if appropriate expression in the fungi after integration into the genome. Multiple constructs including distinct or related target polynucleotides may be added to the fungal cells in a single transformation to obtain integration of multiple target polynucleotides in a single experiment.

Generally, the nomenclature used herein and the laboratory procedures utilized in the present invention include molecular, biochemical, microbiological and recombinant DNA techniques that are well known and commonly employed in the art. Standard techniques are used for cloning. DNA and RNA isolation, amplification and purification. Generally enzymatic reactions involving DNA ligase, DNA polymerase, restriction endonucleases and the like are performed according to the manufacturer's specifications. Such techniques are thoroughly explained in the literature and are generally performed according to methods available to those of skill in the art.

The phrase "nucleic acid" or "polynucleotide sequence" refers to a single-stranded or double-stranded polymer of deoxyribonucleotide or ribonucleotide bases read from the 5' to the 3' end. Nucleic acids may also include modified nucleotides that permit correct read-through by a polymerase and do not alter expression of a polypeptide encoded by that nucleic acid.

A "coding sequence" or "coding region" refers to a nucleic acid molecule having sequence information necessary to produce a gene product, when the sequence is expressed. The phrase "nucleic acid sequence encoding" refers to a nucleic acid which directs the expression of a specific protein or polypeptide. The nucleic acid sequences of this invention include both the DNA strand sequence that is transcribed into RNA and the RNA sequence that is translated into protein. The nucleic acid sequences include both the full length nucleic acid sequences as well as non-full length sequences derived from, the full length sequences. It should be understood that the sequences include the degenerate codons of the native sequence or sequences which may be introduced to provide codon preference in a specific host cell.

The terms "isolated," "purified," or "biologically pure" refer to material that is substantially or essentially free from components that normally accompany it as found in its native state. Purity and homogeneity are typically determined using molecular biology and analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

An "expression cassette" refers to a nucleic acid construct, which when introduced into a host cell, results in transcription and/or translation of a RNA and/or polypeptide, respectively. The expression cassette may include a nucleic acid comprising a promoter sequence, with or without a sequence containing mRNA polyadenylation signals, and one or more restriction enzyme sites located downstream from the promoter allowing insertion of heterologous gene sequences. The expression cassette is capable of directing the expression of a heterologous protein when the gene encoding the heterologous protein is operably linked to the promoter by insertion into one of the restriction sites. The recombinant expression cassette allows expression of the heterologous protein in a host cell when the expression cassette containing the heterologous protein is introduced Into the host cell. Expression cassettes can be derived from a variety of sources depending on the host cell to be used for expression. For example, an expression cassette can contain components derived from a viral, bacterial, insect, plant, or mammalian source. In the case of both expression of transgenes and inhibition of endogenous genes (e.g., by antisense, or sense suppression) the inserted polynucleotide sequence need not be identical and can be "substantially identical" to a sequence of the gene from which it was derived. For example some yeasts belong to the CUG clade which have an alternative codon usage and the polynucleotide must be altered to code for the correct amino acid and ensure that lys/ser are properly incorporated.

The term "recombinant cell" (or simply "host cell") refers to a cell into which a recombinant expression vector containing tire constructs described, herein has been introduced. It should be understood that the term "host cell" is intended to refer not only to the particular subject cell but to the progeny of such a cell Because certain modifications may occur in succeeding generations due to either mutation or environmental influences, such progeny may not, in fact, be identical to the parent cell, but are still included within the scope of the term "host cell" as used herein. Methods for introducing polynucleotide sequences into various types of cells are well known in the art. Provided are host cells or progeny of host cells transformed with the recombinant expression cassettes and constructs of the present invention.

The terms "promoter," "promoter region," or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

As used herein, a polynucleotide is "operably linked," "operably connected," or "operably inserted" when it is placed into a functional relationship with a second polynucleotide sequence. For instance, a promoter is operably linked to a coding sequence if the promoter is connected to the coding sequence such that it may effect transcription of the coding sequence. This same definition is sometimes applied to the arrangement of other transcription control elements (e.g. enhancers, terminators) in an expression cassette. Transcriptional and translational control sequences axe DNA regulatory sequences, such as promoters, enhancers, polyadenylation signals, terminators, and the like, that provide for the expression of a coding sequence in a host cell. Promoters useful in the practice of the present invention include, but are not limited to, constitutive, inducible, temporally-regulated, developmentally regulated, and chemically regulated promoters.

The term "nucleic acid construct" or "DNA construct" is sometimes used to refer to a coding sequence or sequences operably linked to appropriate regulatory sequences and inserted into an expression cassette for transforming a cell or for translating a protein in a cell-free system or for use in homologous recombination. Such a nucleic acid construct may contain a coding sequence for a gene product of interest, and optionally a selectable marker gene and/or a reporter gene. The term "selectable marker gene" refers to a gene encoding a product that, when expressed, confers a selectable phenotype, such as antibiotic resistance, on a transformed cell. The term "reporter gene" refers to a gene that encodes a product which is easily detectable by standard methods, either directly or indirectly. Reporter genes include, but are not limited to luciferases, β-glucuronidase (GUS), fluorescent proteins such as green fluorescent protein (GFP), dsRed, mCherry and others available to those skilled in the art. Selectable markers Include but are not limited to markers that confer resistance to an antibiotic such as kanamycin and hygromycin.

A "heterologous" region of a nucleic acid construct is an identifiable segment (or segments) of the nucleic acid molecule within a larger molecule that is not found in association with the larger molecule in nature. When the heterologous region encodes a gene, the gene will usually be flanked by DNA that does not flank the genetic DNA in the genome of the source organism. In another example, a heterologous region is a construct where the coding sequence itself is not found in nature. The term "DNA construct" is also used to refer to a heterologous region, particularly one constructed for use in transformation of a cell.

The term "vector" is intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, where additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome, such as some viral vectors or transposons. Moreover, certain vectors are capable of directing the expression of genes to which they are operatively linked or connected. Such vectors are referred to herein as "recombinant expression vectors" (or simply, "expression vectors"), In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A "nucleic acid probe" or "oligonucleotide" is defined as a nucleic acid capable of binding to a target nucleic acid of complementary sequence through one or more types of chemical bonds, usually through complementary base pairing, usually through hydrogen bond formation. As used herein, a probe may include natural bases (i.e., A, G, C, or T) or modified bases (7-deazaguanosine, inosine, etc.). In addition, the bases in a probe may be joined by a linkage other than a phosphodiester bond, so long as it does not interfere with hybridization. For example, probes may be peptide nucleic acids (PNAs) in which the constituent bases are joined by peptide bonds rather than phosphodiester linkages, it will be understood that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence (sequence fragment).

Fungi include but are not limited to species of the genera *Fusarium, Aspergillus, Botrytus, Magnapothe, Puccinia, Blumeria, Mycosphaerella, Colletrotichum, Ustilago, Melampsora, Absidia, Acremonium, Alternaria, Candida, Saccharomyces, Phytophthora, Erysiphe, Cladosporium, Cryptococcus, Microsporum, Trichophyton, Epidermophyton, Sporotrix, Trichothecium, Trichophyton, Aureobasidium Stemphylium, Rhizopus, Phoma, Rhodotorula, Penicillium, Paecilomyces, Nigrospora, Mycogone, Neurospora, Mucor, Epicoccum, Helminthosporium, Gliocladium, Geotrichum, Epidermophyton, Drechslera, Cladosporium, Chaetomium, Bipolaris, Scheffersomyces, Pichia, Spathaspora, Komagataella, Agaricus, Phaffia* or *Sclerotinia*. Protists include, but are not limited to *Trypanosoma* and *Euglena*.

Methods of using the constructs provided herein for genome editing, including methods of allele replacement, diploid gene replacement and genetic engineering of fungi or protists. The methods include generating or obtaining the constructs including thymidine kinase, an endonuclease and a recognition site specific for the endonuclease. The constructs are introduced into the fungal or protist cells and selecting for the thymidine kinase by growing the fungus or protists on antifolate containing medium. The antifolate containing medium includes thymidine and an agent selected from methotrexate and/or sulfanilaminde. Additional antifolate agents may be used in place of or in combination with those used herein such as pemetrexed, raltitrexed, or pralatrexate. *Saccharomyces* cells should be grown out on media with a non-fermentable carbon source or the mitochondria may be lost and petite cell formation will dominate the transformants. Growing the cells on antifolate containing medium containing glycerol overcame loss of the mitochondria. Other non-fermentable carbon sources can also be used and these include but are not limited to ethanol and lactate. The selection in antifolate selects for integration of the construct Into the genome as demonstrated in the Examples below. The Integration of the construct may result in deletion of the gene at the site of insertion, replacement of the gene with a distinct allele of the same gene, or integration of a novel gene or set of genes. The result will depend on the specifics of the construct used in the methods. Those of skill in the art will understand how to design constructs for specific uses based on the methods and examples provided herein. The constructs may be introduced into the fungal or protists cells using any means available to those of skill in the art and includes but is not limited to transformation, transduction, and electroporation. Selection involves growing the fungus or protists on media containing agents that allow for selection of expression (or lack thereof) of the polynucleotides in the constructs.

The integrated construct including thymidine kinase can be removed from the yeast genome by inducing the expression of the nuclease and selecting the cells in the presence of an agent that becomes toxic in the presence of thymidine kinase. The agent may be 5'-fluorodeoxyuridine (FUdR) as used in the Examples or may be selected from acyclovir, valacyclovir, famcyclovir, pencyclovir or combinations of any of these agents. After selection, the cells may be assessed for the loss of thymidine kinase by a method including, but not limited to susceptibility to the toxic agent, the inability to grow in antifolate media or via genetic analysis of the resulting cells.

The methods described herein may also be used with diploid cells to effect integration onto both alleles of the fungus. As described above and in the Examples, two constructs with different selectable markers may be introduced into a cell and the diploid integration can be selected for by selecting for cells with antifolate media and both selectable markers. The diploid cells resulting from integration of the constructs can be rescued to the wild-type or starting cell phenotype by inducing the nuclease to cause a double-strand break (DSB) and then counterselecting for loss of the thymidine kinase using the toxic agent as described above. The resulting cells should lack the selectable markers and should be unable to grow on antifolate media.

Fungal organisms, in particular *Saccharomyces cerevisiae*, have been engineered previously to produce valuable fuel and commodity compounds. For example, metabolic networks enabling use of novel carbon sources, such as xylose, have also been installed to varying degrees of success. Part of the difficulties with these systems is the efficiency of selecting for engineered yeast when many potentially useful yeast are diploid. Here we describe the use of the HERP series of *Saccharomyces* genome editing cassettes. The HERP cassettes are composed of a novel positively and negatively selectable marker, TkMX (derived from human herpes simplex virus thymidine kinase), an inducible double-strand break generator in the form, of a meganuclease and its cut site, and multiple secondary markers. As described above, these cassettes allow for manipulation of a genomic locus at rates approaching 1% of surviving cells, or approximately 1000× more efficiently than currently reported CRISPR/Cas9 rates in wild *Saccharomyces* species.

Figure 7:
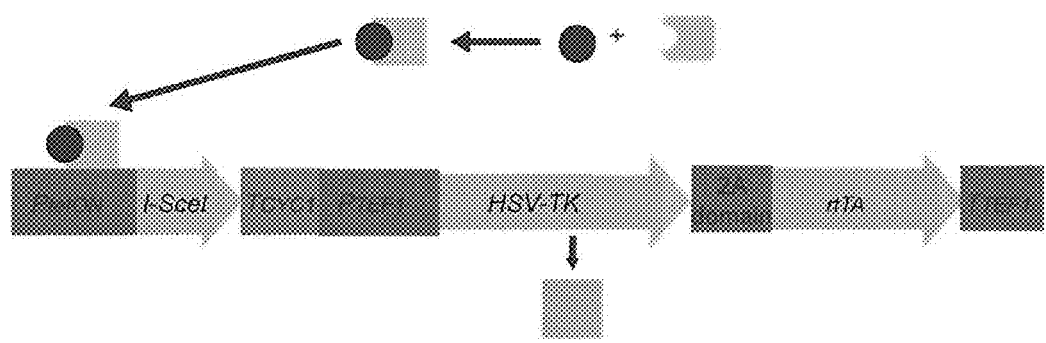
FIG. 7 is a schematic showing the HERP2.0 cassette. The GAL1 promoter used to induce expression of the I-SceI meganuclease in the HERP1.x was replaced with the tetON promoter, a minimal CYC1 promoter core possessing tetracycline-responsive elements (TREs). The tetracycline-responsive activator (rtTA) was fused to the 3' end of the TK gene via a viral 2A domain, which causes the translating ribosome to "skip" producing two separate polypeptides from one mRNA. The rtTA protein, independent from the TK protein, is able to bind to tetracycline or a similar drug and induce 1-SceI expression.

The HERP2.0 cassette is an additional improvement that allows for selection in other fungal organisms. The HERP 2.0 cassette HERP2.0 has an experimental efficiency of 0.0035% and is shown in FIG. 7. The purpose of HERP2.0 is to mimic the UAU system from *Candida albicans* in *Saccharomyces*, which would make the deletion and replacement of a genomic locus with sequences of Interest take less time. HERP2.0 is more complex than the HERP1.x series. Briefly, a tetracycline-responsive transcription factor was fused to the 3' end of the thymidine kinase gene via a "2A domain" from an enterovirus, which functions to make the translating ribosome "skip" and cause two separate peptides to be made from one mRNA. Also, the SCEI meganuclease gene I used in the HERP1.x cassettes is now driven by a tetracycline-inducible promoter, and a terminator from the CYC1 gene is attached to SCEI. The initial data for this construct demonstrates high efficiency and we have been able to delete a gene using it, and replace the gene with an efficiency of 0.0035% of cells surviving the transformation. This rate is about 100× better than typical gene insertions and 3× better than published yeast CRISPR/Cas9 rates in the yeasts strains tested.

The system described herein may also be used for production of a library of parts, mostly derived from diverse yeast species requiring genome-wide alterations to their codons, to expedite recombinatorial engineering for the production of bio fuels from lignocellulosic biomass. These parts are designed to be screened on plasmids, assembled onto plasmids in user-specified or random combinations, and stably integrated into the *Saccharomyces* genome via HERP technology. These cassettes may contain a unique barcode segment to identify the cassette, universal PCR primer binding sites to allow easy amplification and PCR based cloning, an asymmetric loxP site and two rare cutting restriction enzyme sites for future modifications via gap repair cloning (such as NotI and SfiI). Those of skill in the art will appreciate that other rare cutting restriction endonuclease sites can be incorporated. The ORFs chosen for Inclusion were from a variety of sources deemed important for biofuel production, but open reading frames useful for other applications could also be included in this design for rapid integration. The cassettes can be assembled, to produce diverse combinatorial metabolic networks to establish metabolic pathways.

Figure 8:
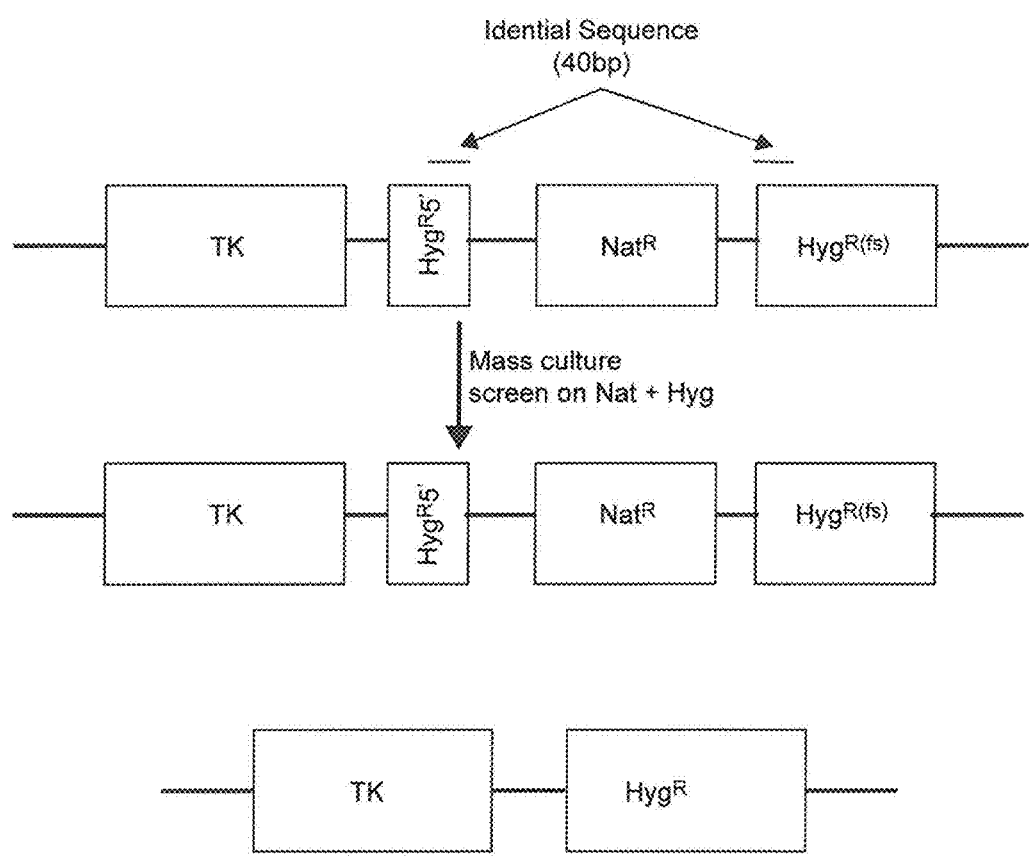
FIG. 8 is a schematic diagram showing the construction of the DERP cassette. The DERP cassette has the herpes simplex virus TK gene followed by the 5' end of the hygromycin gene. The hygromycin gene 5' end is followed by the nourceothricin resistance gene (nat) and a copy of the hygromycin missing a portion of the 5' end of the gene. The integration onto the first chromosome is selected by culturing on Nat and once integrated, double drug selection with Hyg and Nat will select for recombination between the portions of the hygromycin gene segments, loss of the nat gene on one chromosome and integration of TK on both chromosomes of the diploid organism as shown in the bottom, portion of the figure.

The DERP cassette is shown in FIG. 8 and can be inserted into one locus of a chromosome of a diploid cell by selecting for nourceothricin resistance. This results in a heterozygous cell containing DERP on one chromosome and the native locus on the other. Once insertion is confirmed, this intermediate strain is cultured in rich media plus nourceothricin, then plated onto double drag plates with nourceothricin and hygromycin. The double drug plates select for a series of events: on occasion gene conversion between the chromosomes will occur, resulting in a cell that is homozygous for the DERP insertion. A subset of these cells will also "cross out" the nat gene and restore the hyg gene due to the engineered repeat as designated in the schematic (FIG. 8). The result is that some small population of cells in a culture will automatically delete the second copy of the gene knocked out originally by the DERP cassette and this can be selected for by the double drug plates.

The constructs used in this method comprise a first promoter operably connected to a first polynucleotide encoding a thymidine kinase, a second promoter operably connected to a second polynucleotide encoding a 5' portion of a first selectable marker, a third promoter operably connected to a third polynucleotide encoding a second selectable marker and a fourth polynucleotide encoding a 3" portion of the first selectable marker. The second polynucleotide and the fourth polynucleotide encoding the 5' portion and the 3' portion of the first selectable marker contain a region of overlapping sequence to allow for recombination between the 5' portion and the 3' portion of the polynucleotide sequence encoding the first selectable marker. The overlapping or repeated sequences of the polynucleotides encoding the first selectable marker may overlap by at least 20 nucleotides (i.e. share a 20 nucleotide sequence). The overlapping section of nucleotides may be longer, for example 25, 30, 35, 40, 45, 50 or more nucleotides to allow for more efficient recombination between the 5" portion of the second polynucleotide and the 3' portion of the second polynucleotide.

Methods of using these constructs for genome editing, allele replacement or genetic, engineering of fungus or protists are also provided. The constructs described herein may be introduced into a fungal or protist cell and then integration into the genome of the cell can be selected for the selecting for thymidine kinase as described above and selecting for expression of the second selectable marker, i.e. by growing the cells in media comprising an antibiotic or other agent to which the cells are susceptible and will not grow in the absence of the selectable marker but to which the selectable marker confers resistance and allows growth of the cells in the presence of the antibiotic or other agent. The selection step allows isolation of engineered fungal or protist cells incorporating at least a portion, of the construct comprising at least the polynucleotide encoding the thymidine kinase at the second selectable marker onto at least one chromosome or allele. The methods may further comprise selecting the engineered fungal or protist cells for the first selectable marker and the second selectable marker to allow selection and isolation of engineered fungal or protist cells comprising at least a portion of the construct integrated into both alleles. This method allows one of skill in the art to knockout both copies of a gene in a diploid organism or to engineer both copies of a gene of interest to avoid having to account for allele affects.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential, to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value felling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms pat of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Primers, Strains, and Media

Strains used or created by this work are noted in Table 1. Primers used and their sequences are noted in Table 2. For general culturing of strains in this work, either YPD (1% yeast extract, 2% peptone, 2% glucose) or SC (0.17% yeast nitrogen base, 0.5% ammonium sulfate, 0.2% complete drop out mix, 2% glucose) media was used. Prior to galactose induction, cells were grown overnight in medium consisting of 2% yeast extract, 4% peptone, 100 mg/L adenine hemisulfate, and 0.2% glucose. Galactose induction was performed in 2% yeast extract, 4% peptone, 100 mg/L adenine hemisulfate, and 4% galactose. TK selection was done on YPGly+ antifolates (YPGly+AF, 1% yeast extract, 2% peptone, 200 µg/mL methotrexate, 5 mg/mL sulfanilamide, 5 mg/mL thymidine, and 50 µg/mL hypoxanthine). For counterselection, 50 µg/mL 5-fluorodeoxyuridine was added to SC medium (SC+FUdR); double replacement in diploids substituted the glucose in this formula with 5% glycerol (SCGly+FUdR), For double replacement in diploids, YPD plates with 300 µg/ml, hygromycin or 400 µg/mL G418 were used. Solid medium was formed by the addition of 1.8% agar to all media formulations before autoclaving.

TABLE 1

Strains used in this work.

| Strain Name | Species | Genotype | References |
|---|---|---|---|
| CBS 7001 | Saccharomyces uvarum | MATa/MATα | 1 |
| FM1098 | Saccharomyces kudriavzevii | MATa hoΔ::NatMX | 2 |
| FM1282 | Saccharomyces cerevisiae | MATa ura3-Δ lys2-Δ $P_{TDH3}$-yEGFP-$T_{CYC1}$ | 3 |
| JRY9190 | Saccharomyces uvarum | MATα hoΔ::NatMX | 1 |
| JRY9288 | Saccharomyces mikatae | MATα hoΔ::NatMX | Gift from Jasper Rine's Lab |
| M22 | Saccharamyces cerevisiae | MATa/MATα | 4 |

TABLE 1-continued

Strains used in this work.

| Strain Name | Species | Genotype | References |
|---|---|---|---|
| RM11-1a | Saccharomyces cerevisiae | MATa leu2-Δ ura3-Δ hoΔ::KanMX | 5 |
| W303-1a | Saccharomyces cerevisiae | MATa leu2-3,112 trp1-1 can1-100 ura3-1 ade2-1 his3-11,15 | 6 |
| yHWA52 | Saccharomyces cerevisiae | MATa URA3::TK-hENT1 leu2-3,112 trp1-1 can1-100 ade2-1 his3-11,15 | This work |
| yHWA189 | Saccharomyces uvarum | MATα hoΔ::TkMX | This work |
| yHWA192 | Saccharomyces kudriavzevii | MATa hoΔ::TkMX | This work |
| yHWA195 | Saccharomyces kudriavzevii | MATa hoΔ | This work |
| yHWA204 | Saccharomyces mikatae | MATa hoΔ::TkMX | This work |
| yHWA241 | Saccharomyces cerevisiae | MATa ade2-Δ::TkMX-URA3 leu2-Δ ura3-Δ hoΔ::KanMX | This work |
| yHWA245 | Saccharomyces cerevisiae | MATa ade2-Δ::HERP1.0 leu2-Δ ura3-Δ hoΔ::KanMX | This work |
| yHWA247 | Saccharomyces cerevisiae | MATa ade2-Δ::HERP1.1 leu2-Δ ura3-Δ hoΔ:KanMX | This work |
| yHWA267 | Saccharomyces cerevisiae | MATa/MATα ade2-Δ::HERP1.1/ADE2 | This work |
| yHWA272 | Saccharomyces cerevisiae | MATa ura3-Δ lys2-Δ ade2-Δ::HERP1.1 $P_{TDH3}$-yEGFP-$T_{CYC1}$ | This work |
| yHWA275 | Saccharomyces cerevisiae | MATa ura3-Δ lys2-Δ ade2-Δ::HERP1.2 $P_{TDH3}$-yEGFP-$T_{CYC1}$ | This work |
| yHWA279 | Saccharomyces cerevisiae | MATa/MATα ade2Δ::HERP1.1/ade2Δ::HERP1.2 | This work |
| yHWA285 | Saccharomyces uvarum | MATa/MATα chrV::HERP1.1/+ | This work |
| yHWA292 | Saccharomyces uvarum | MATa/MATα chrV::HERP1.1/chrV::HERP1.2 | This work |

References cited in Table 1:
1. Scannell, D. & Zill, O. The awesome power of yeast evolutionary genetics: new genome sequences and strain resources for the Saccharomyces sensu stricto genus. G3 Genes|Genomes|Genetics 1, 11-25 (2011).
2. Hittinger, C. T. Remarkably ancient balanced polymorphisms in a multi-locus gene network. Nature 464, 54-8 (2010).
3. Hittinger, C. T. & Carroll, S. B. Gene duplication and the adaptive evolution of a classic genetic switch. Nature 449, 677-81 (2007).
4. Mortimer, R. K. Evolution and Variation of the Yeast (Saccharomyces) Genome. Genome Res. 10, 403-409 (2000).
5. Brem, R., Yvert, G., Clinton, R. & Kruglyak, L. Genetic dissection of transcriptional regulation in budding yeast. Science (80-.). 296, 752-5 (2002).
6. Veal, E. A., Ross, S. J., Malakasi, P., Peacock, E. & Morgan, B. A. Ybp1 is required for the hydrogen peroxide-induced oxidation of the Yap1 transcription factor. J. Biol. Chem. 278, 30896-904 (2003).

TABLE 2

Oligonucleotides used in this work.

| Primer # | Primer name | Primer sequence | Uses |
|---|---|---|---|
| oHWA130 | TkMX F WGA | CTAGGATACAGTTCTCACATCACAT CCGAACATAAACAACCATGGCTTCG TACCCCTGCC (SEQ ID NO: 7) | insertion of TK into the MC promoter/terminator pair |
| oHWA131 | TkMX R WGA | AGTTCTTGAAAACAAGAATCTTTTT ATTGTCAGTACTGATCAGTTAGCCT CCCCCATCTC (SEQ ID NO: 8) | insertion of TK into the MX promoter/terminator pair |

TABLE 2-continued

Oligonucleotides used in this work.

| Primer # | Primer name | Primer sequence | Uses |
|---|---|---|---|
| oHWA150 | Suva-HO:-843F WGA | TGTAAATTCACACACGAGTGTCACG (SEQ ID NO: 9) | Confirmation of TkMX insertion into hoΔ::NatMX locus of S. uvarum |
| oHWA151 | Suva-HO:+2011R WGA | AAAACTTTTGTTTGCATTCATTATATCG (SEQ ID NO: 10) | Confirmation of TkMX insertion into hoΔ::NatMX locus of S. uvarum |
| oHWA153 | pDERP::I-SceI R WGA | CGAGGCAAGCTAAACAGATCTCTAGACCTATTATTTCAGGAAAGTTTCGGAGGAGATAG (SEQ ID NO: 11) | Construction of HERP1.0 |
| oHWA154 | pDERP::TEF F WGA | CTATCTCCTCCGAAACTTTCCTGAAATAATAGGTCTAGAGATCTGTTTAGCTTGCCTCG (SEQ ID NO: 12) | Construction of HERP1.0 |
| oHWA156 | pDERP::hyg frag 1 F WGA | AGATGGGGGAGGCTAACGGAGGTGGAGGTGGAGGTGGAGGTATGGGTAAAAAGCCTGAAC (SEQ ID NO: 13) | Construction of HERP1.1 |
| oHWA163 | pTKKanMX::Kan F WGA | GAGATGGGGGAGGCTAACGGAGGTGGAGGTGGAGGTGGAGGTATGGGTAAGGAAAAGAC (SEQ ID NO: 14) | Construction of HERP1.2 |
| oHWA169 | pDERP::TEF R WGA | CAGCTCCCGGAGACGGTCACAGCTTGTCTGTAAGCGGATGGAGCTCGTTTTCGACACTGG (SEQ ID NO: 15) | Construction of HERP1.0 |
| oHWA200 | pUC19::TkMX F #2 | CAGTCACGACGTTGTAAAACGACGGCCAGTGAATTCAGATCTGTTTAGCTTGCCTTGTCC (SEQ ID NO: 16) | Insertion of TkMX marker into pUC19 vector |
| oHWA201 | pUC19::TkMX R #2 | GGTCGACTCTAGAGGATCCCCGGGTACCGAGCTCGAATTCGAGCTCGTTTTCGACACTGG (SEQ ID NO: 17) | Insertion of TkMX marker into pUC19 vector |
| oHWA217 | TK-URA3 F | CGCCGCCATCCAGTGTCGAAAACGAGCTCGATTCGGTAATCTCCGAACAGAAGGAAGAAC (SEQ ID NO: 18) | Construction of S. cerevisiae RM11-1a ade2Δ::TkMX-URA3 strain |
| oHWA218 | TK-URA3 R | GTTCTTCCTTCTGTTCGGAGATTACCGAATCGAGCTCGTTTTCGACACTGGATGGCGGCG (SEQ ID NO: 19) | Construction of S. cerevisiae RM11-1a ade2Δ::TkMX-URA3 strain |
| oHWA230 | MX marker swap F WGA | AAACGCTCCCCTCACAGACG (SEQ ID NO: 20) | Used to replace NatMX with TkMX |
| oHWA231 | MX marker swap R WGA | CTGGGCAGATGATGTCGAGG (SEQ ID NO: 21) | Used to replace NatMX with TkMX; construction of HERP1.1 and HERP1.2 |
| oHWA236 | pHEEP-Gal::Pgal1 F WGA | TTACCCAACTTAATCGCCTTGCAGCACATCCCCCCTTGGATGGACGCAAAGAAGTTTAAT (SEQ ID NO: 22) | Construction of HERP1.0 |
| oHWA263 | Suva-HO:-88F WGA | CTCTTAGCCCTTTCTTCTTTCC (SEQ ID NO: 23) | Sequencing of TkMX insertion into hoΔ::NatMX locus of S. uvarum |
| oHWA264 | Suva-HO::+1900R WGA | CCTGCAAATACTGTTCTGACAG (SEQ ID NO: 24) | Sequencing of TkMX insertion into hoΔ::NatMX locus of S. uvarum |
| oHWA265 | Smik-HO:-168F WGA | ACCGTTGAAGCCTATTGAAG (SEQ ID NO: 25) | Confirmation of TkMX insertion into hoΔ::NatMX locus of S. mikatae |
| oHWA266 | Smik-HO:+2010R WGA | TTTAACAGAACGTAGCGTAGC (SEQ ID NO: 26) | Confirmation of TkMX insertion into hoΔ::NatMX locus of S. mikatae |

TABLE 2-continued

Oligonucleotides used in this work.

| Primer # | Primer name | Primer sequence | Uses |
|---|---|---|---|
| oHWA267 | Smik-HO:-62F WGA | TAATCATAAAATTCAAACCTGTATCCC (SEQ ID NO: 27) | Sequencing of TkMX insertion into hoΔ::NatMX locus of S. mikatae |
| oHWA268 | Smik-HO:+1838R WGA | GAATTAAAAATAGCCATTATCATCC (SEQ ID NO: 28) | Sequencing of TkMX insertion into hoΔ::NatMX locus of S. mikatae |
| oHWA290 | Suva-chr5 F WGA | GAAAATAACAAAAAGAAGAAAATGGG (SEQ ID NO: 29) | Confirmation of insertions into chromosome 5 of S. uvarum |
| oHWA291 | Suva-chr5 R WGA | GTTAGGGATATTCTAGTAAAAAAATGC (SEQ ID NO: 30) | Confirmation of insertions into chromosome 5 of S. uvarum |
| oHWA304 | pHERP-X #2 F WGA | ATCCTCTAGAGTCGACTTGGATGGACGCAAAGAAGTTTAATAATCATATTACATGGC (SEQ ID NO: 31) | Insertion of HERP cassettes into pUC19 vector |
| oHWA305 | pHERP-X #2 R WGA | ATGCCTGCAGGTCGACGAGCTCGTTTTCGACACTGGATGG (SEQ ID NO: 32) | Insertion of HERP cassettes into pUC19 vector |
| oHWA306 | ScerRM11-1a-ADE2:I-SceI:HERP F WGA | TAGGTATATCATTTTATATTATTTGCTGTGCAAGTATATCAATAAACTTATATATAGGGATAACAGGGTAATGTCGACTTGGATGGACGC (SEQ ID NO: 33) | Insertion of HERP cassettes into ADE2 locus of S. cerevisiae strain RM11-1a or M22 |
| oHWA307 | ScerRM11-1a-ADE2:HERP R WGA | AGAAAAACAAGAAAACCGGACAAAACAATCAAGTGAGCTCGTTTTCGACACTGGTGGCG (SEQ ID NO: 34) | Insertion of HERP cassettes into ADE2 locus of S. cerevisiae strain RM11-1a or M22 |
| oHWA308 | Scer-RM11-1a-ADE2-_::TK-URA3 F | TTATTTGCTGTGCAAGTATATCAATAAACTTATATAAGATCTGTTTAGCTTGCCTTGTCC (SEQ ID NO: 35) | Construction of S. cerevisiae RM11-1a ade2Δ::TkMX-URA3 strain |
| oHWA309 | Scer-RM11-1a-ADE2-_::TK-URA3 R | AAAACAAGAAAACCGGACAAAACAATCAAGTGGTAATAACTGATATAATTAAATTGAAGC (SEQ ID NO: 36) | Construction of S. cerevisiae RM11-1a ade2Δ::TkMX-URA3 strain |
| oHWA310 | Scer-RM11-1a-ADE2:-143F WGA | GTATGAAATTCTTAAAAAAGGACACC (SEQ ID NO: 37) | Confirmation of ADE2 replacement in RM11-1a or M22 strains of S. cerevisise |
| oHWA311 | Scer-RM11-1a-ADE2:-111F WGA | CGTTGATTTCTATGTATGAAGTCC (SEQ ID NO: 38) | Sequencing primer of ADE2 locus in RM11-1a or M22 strains of S. cerevisiae |
| oHWA312 | Scer-RM11-1a-ADE2:+1809 R WGA | TAAATTGGTGCGTAAAATCGTTGG (SEQ 1D NO: 39) | Sequencing primer of ADE2 locus in M11 in or M22 strains of S. cerevisiae |
| oHWA313 | Scer-RM11-1a-ADE2:+1844 R WGA | AACTAAATGGACAATATTATGGAGC (SEQ ID NO: 40) | Confirmation of ADE2 replacement in RM11-1a or M22 strains of S. cerevisiae |
| oHWA326 | ScerPE-2-ADE2::Suva-ADE2 F WGA | CAATCAAGAAAAACAAGAAAACCGGACAAAACAATCAAGTATGGATTCTAGAACTGTCGG (SEQ ID NO: 41) | Replacement of HERP cassette in RM11-1a with S. uvarum ADE2 ORF |
| oHWA327 | ScerPE-2-ADE2::Suva-ADE2 R WGA | TATTTGCTGTGCAAGTATATCAATAAACTTATATATTATTTGTTTCCTAAATAAGCTTCG (SEQ ID NO: 42) | Replacement of HERP cassette in RM11-1a with S. uvarum ADE2 ORF |

TABLE 2-continued

Oligonucleotides used in this work.

| Primer # | Primer name | Primer sequence | Uses |
|---|---|---|---|
| oHWA328 | RM11-1a ADE2 mPCR F WGA | AATCAAGAAAAACAAGAAAACCGGA CAAAACAATCAAGTATGGATTCTAG AACAGTTGGT (SEQ ID NO: 43) | Replacement of HERP cassette in RM11-1a with S. cerevisiae ADE2 ORF |
| oHWA329 | RM11-1a ADE2 mPCR R WGA | TTATTTGCTGTGCAAGTATATCAAT AAACTTATATATTACTTGTTTTCTA GATAAGCTTC (SEQ ID NO: 44) | Replacement of HERP cassette in RM11-1a with S. cerevisiae ADE2 ORF |
| oHWA342 | ADE2 Allele Swap C > A, M F WGA | CAATCAAGAAAAACAAGAAAACCGG ACAAAACAATCAAGTATGGATTCTA GAACAGTCGG (SEQ ID NO: 45) | Replacement of HERP cassette in RM11-1a with S. arbicola or S. mikatae ADE2 ORF |
| oHWA343 | ADE2 Allele Swap C > E F WGA | CAATCAAGAAAAACAAGAAAACCGG ACAAAACAATCAAGTATGGATTCTA GAACTGTCGG (SEQ ID NO: 46) | Replacement of HERP cassette in RM11-1a with S. eubayanus ADE2 ORF |
| oHWA344 | ADE2 Allele Swap C > K, P F WGA | CAATCAAGAAAAACAAGAAAACCGG ACAAAACAATCAAGTATGGATTCTA GAACAGTTGG (SEQ ID NO: 47) | Replacement of HERP cassette in RM11-1a with S. kudriavzevii or S. paradoxus ADE2 ORF |
| oHWA345 | ADE2 Allele Swap C > A R WGA | ATATTATTTGCTGTGCAAGTATATC AATAAACTTATATACTATTTGTTTT CTAAATAAGC (SEQ ID NO: 48) | Replacement of HERP cassette in RM11-1a with S. arbicola ADE2 ORF |
| oHWA346 | ADE2 Allele Swap C > E R WGA | ATATTATTTGCTGTGCAAGTATATC AATAAACTTATATATTATTTGTTTC CTAAATAAGC (SEQ ID NO: 49) | Replacement of HERP cassette in RM11-1a with S. eubayanus ADE2 ORF |
| oHWA347 | ADE2 Allele Swap C > K R WGA | ATATTATTTGCTGTGCAAGTATATC AATAAACTTATATATTATTTGCTTT CTAAATAAGC (SEQ ID NO: 50) | Replacement of HERP cassette in RM11-1a with S. kudriavzevii ADE2 ORF |
| oHWA348 | ADE2 Allele Swap C > M R WGA | ATATTATTTGCTGTGCAAGTATATC AATAAACTTATATACTATTTGTTTT CTAAGTAAGC (SEQ ID NO: 51) | Replacement of HERP cassette in RM11-1a with S. mikatae ADE2 ORF |
| oHWA349 | ADE2 Allele Swap C > P R WGA | ATATTATTTGCTGTGCAAGTATATC AATAAACTTATATATTATTTGTTTT CTAAATAAGC (SEQ ID NO: 52) | Replacement of HERP cassette in RM11-1a with S. Paradoxus ADE2 ORF |
| oHWA352 | Scer-S288c-ADE2-_:: HERP F WGA | TTTATAATTATTTGCTGTACAAGTA TATCAATAAACTTATATATAGGGAT AACAGGGTAATTTGGATGGACGCAA AGAAGTTTAATAATC (SEQ ID NO: 53) | Insertion of HERP cassettes into ADE2 locus of S. cerevisiae strain 2288c |
| oHWA353 | Scer-S288c-ADE2-_:: HERP R WGA | CAAGAAAAACAAGAAAATCGGACAA AACAATCAAGTATTAAGGGTTCTCG AGAGCTCGTT (SEQ ID NO: 54) | Insertion of HERP cassettes into ADE2 locus of S. cerevisiae strain S288c |
| oHWA373 | Suva-chr5:HERP1.X F WGA | GAAAGAAAAGTCAGCATACCGGTTT TCACTTCTGTATATAGGGATAACAG GGTAATTTGG (SEQ ID NO: 55) | insertion of HERP cassettes into chromosome 5 of S. uvarum strain CBS7001 |
| oHWA374 | Suva-chr5:HERP1.X .X R WGA | TTAAAAAATGTAGGTAGGTGAGTAG GTAGGTCAAAAGAAATTAAGGGTTC TCGACAGCTC (SEQ ID NO: 56) | Insertion of HERP cassettes into chromosome 5 of S. uvarum strain CBS7001 |

TABLE 2-continued

Oligonucleotides used in this work.

| Primer # | Primer name | Primer sequence | Uses |
| --- | --- | --- | --- |
| oHWA375 | Suva-chr5:yEGFP F WGA | AAGAAAAGTCAGCATACCGGTTTTC ACTTCTGTATAGTTCGAGTTTATCA TTATCAATAC (SEQ ID NO: 57) | Replacement of HERP cassette in CBS7001 with yEGFP |
| oHWA376 | Suva-chr5:yEGFP R WGA | TTAAAAAATGTAGGTAGGTGAGTAG GTAGGTCAAAAGAAGAGTGTAAACT GCGAAGCTTG (SEQ ID NO: 38) | Replacement of HERP cassette in CBS7001 with yEGFP |
| oHWA377 | Suva-chr5 F Seq WGA | ACAAGAAAGAAAAGTCAGCATACC (SEQ ID NO: 59) | Sequencing of insertions into chromosome 5 of S. uvarum |
| oHWA378 | Suva-chr5 R Seq WGA | TAGATAATAATATAATAATTTAAC GGAGG (SEQ ID NO: 60) | Sequencing of insertions into chromosome 5 of S. uvarum |
| OM8330 | S. kud. HO 1 | TTTGCTTTCGGTGTACATTTG (SEQ ID NO: 61) | Confirmation of TkMX insertion into hoΔ::NatMX locus of S. kudriavzevii |
| OM8331 | S. kud. HO 2 | GTCAGCTGCACTGCGTTTTA (SEQ ID NO: 62) | Confirmation of TkMX insertion into hoΔ::NatMX locus cf S. kudriavzevii |
| OM8332 | S. kud. HO 3 | CACGACATCAATGGCGTAAA (SEQ ID NO: 63) | Sequencing of TkMX insertion into hoΔ::NatMX locus of S. kudrializevii |
| OM8333 | S. kud. HO 4 | TATTCAGGTAAAGCCGCAGAA (SEQ ID NO: 64) | Sequencing of TkMX insertion into hoΔ::NatMX locus of S. kudriavzevii |

Transformation of *Saccharomyces*.

The lithium acetate/PEG-4000 method (51) with species-specific temperature modifications (5) and two separate electroporation methods (45, 52) were used.

Construction of Strains and Plasmids

TK-hENT1:

plasmid p306-BrdU-Inc (1) was linearized with StuI and transformed into W303-1a (2) using the lithium acetate/PEG-4000 method. The transformation was selected on SC-uracil media, and candidates were confirmed by sequencing.

TkMX:

The gene encoding thymidine kinase was amplified from plasmid p306-BrdU-Inc using oHWA130/131. This PCR product was used to transform the S. uvarum strain JRY9190 (3), which was subsequently selected on YPD+antifolate drugs to give yHWA71. oHWA200/201 were used to amplify TkMX and to provide EcoRI sites on either end, which were then used to Insert TkMX into the EcoRI site in plasmid pUC19, forming pHWA01. TkMX was then inserted into the hoΔ::NatMX loci of S. mikatae strain JRY9288 and S. kudriavzevii strain FM1098 (4) by amplifying the TK gene from pHWA01 using oHWA230/231 and selecting on YPGly+AF media, forming yHWA204 and yHWA192, respectively. Once insertion was confirmed by sequencing, yHWA192 culture was spread onto SC media, grown overnight, and replica-plated to SCGly+FUdR plates. Recovered strains were sequenced to confirm the removal of TkMX crossing over at the direct repeats flanking the cassette. The ADE2 gene of RM11-1a was replaced using TkMX PCR product amplified from pHWA01 with primers oHWA216/218 along with URA3 amplified from pRS316 with primers oHWA217/219 and selected on YPGly+AF plates. These resulting ade2Δ::TkMX-URA3 strains were then transformed with ADE2 PCR product amplified from S. uvarum strain CBS 7001 (3) using the Phusion polymerase kit (New England Biolabs, Ipswitch, Mass., USA) with primers oHWA298/299.

HERP 1.0:

TkMX was amplified from yHWA71 with oHWA154/169, and $P_{GAL1}$-SCEI was amplified from pGSKU (5) with oHWA153/236. Plasmid pRS316 (6) was digested with NcoI, dephosphorylated, and then transformed into S. cerevisiae strain FM1282 (7), along with the TkMX and the $P_{GAL1}$-SCEI PCR products. Transformants were selected on YPD+antifolate drugs. Resulting yeast colonies were pooled, and their DNA was extracted. Plasmid DNA was recovered into DH5α E. coli cells (New England. Biolabs) by electroporation and plating onto LB+carbenicillin. Bacterial clones were screened by PCR for correctly sized insertions into pRS316, and the insertions were confirmed by sequencing, resulting in pHWA12. The HERP1.0 cassette was amplified from pHWA12 with oHWA304/305 and subcloned into the SalI site of pUC19 (8) to form pHERP1.0.

HERP1.1:

HERP 1.0 was amplified from pHWA16 with oHWA306/307, which targeted it to delete the ADE2 gene in S. cerevisiae strain RM11-1a and inserted the I-SceI cut site adjacent to the $P_{GAL1}$ promoter, resulting in strain yHWA245. The hygromycin resistance gene Hyg (hph, hygromycin B phosphotransferase) was amplified from pAG32 (9) with oHWA156/231, which added an 8× Gly linker to the 5' end of Hyg and targeted the PCR product to insert into the 3' end of HSV-TK. This PCR product was used to transform yHWA245, which was selected on YPD+hyg media. Resistant colonies were screened by PCR for insertion into the HERP1.0 cassette ADE2, and this was confirmed by sequencing, giving strain yHWA247. The HERP1.1 cassette was amplified from pHWA12 with oHWA304/305 and subcloned by A-tailing with standard Taq polymerase (New England Biolabs, Ipswich, Mass.) then using the pGEM-T Easy Vector System (Promega, Madison, Wis.) to form pHERP1.1.

HERP 1.2:

HERP 1.1 was inserted into the ADE2 locus of S. cerevisiae strain FM1282 by amplifying the cassette from genomic DNA of yHWA247 with oHWA352/353 and selecting on YPD+hyg media, resulting in yHWA272. Once insertion was confirmed, the G418-resistance gene (Kan) from pUG6 (10) was amplified using primers oHWA163/231, which added the same 8× Gly linker and targeted it to the same area previously used to make the Hyg fusion. The PCR product was used to transform yHWA272, which was selected on YPD+G418, Resulting colonies were screened by PCR for changes in size, and candidates were confirmed by sequencing, resulting in strain yHWA275. The HERP1.2 cassette was amplified from pHWA12 with oHWA304/305 and subcloned by A-tailing with standard Taq polymerase then using the pGEM-T Easy Vector System to form pHERP1.2.

Selection of TK-Based Genome Integration.

For evaluation of p306-BrdU-Inc transformations, or TkMX or HERP1.0 integration selections, transformation reactions were plated onto YPGly+AF. For HERP cassettes with drug fusions, transformations were plated onto YPD+200 mg/L hyg, YPD+300 mg/L G41.8, or YPD+hyg+G418, Candidate transformants were struck out for single colonies on fresh plates using the appropriate drug combination, and insertion was confirmed using colony PCR and sequencing insertion junctions.

Induction of HERP Cassette.

The day prior to transformation, strains possessing the integrated HERP cassette were inoculated from a single colony to pre-induction media and grown overnight. The following day, 25 mL of induction media was inoculated to a 600 nm optical density ($OD_{600}$) of 0.25 (for LiAc/PEG) or 0.3 (for electroporation). These cultures were shaken at 250 rpm in the optimum temperature for the strain or species until the appropriate $OD_{600}$ reading for the transformation protocol in use was reached.

Selection of Replacement of TkMX or the HERP Cassette.

After transformation via electroporation, cells were plated onto SC medium and incubated at optimum temperature for at least 24 hours. These plates were then placed at 4° C. for an hour then replicated to SC+FUdR. The replicated plates were grown at the optimal temperature for that species or strain, occasionally being re-replicated to fresh FUdR plates if background growth was too high to pick distinct colonies. Candidate transformants were struck out for isolated colonies on fresh FUdR plates and confirmed by colony PCR and tetrad analysis.

Results

The Loss of Thymidine Kinase in Fungi Created a Natural Auxotrophy.

Due to the challenges of porting existing high-efficiency genome editing techniques to non-laboratory strains of S. cerevisiae and relatives, we sought to design a technique that could be used in any Saccharomyces species or strain. The enzyme thymidine kinase (Tk) functions in the pyrimidine salvage pathway to convert the nucleoside thymidine to thymidine monophosphate (dTMP). Although present in a wide range of organisms from herpesvirus to humans, no fungal TK genes or enzymatic activities have been identified to date. Analysis of several key genome sequences suggests that TK was indeed lost early in the fungal lineage after it split from the animal lineage about a billion years ago (FIG. 1); some protist lineages have also independently lost TK.

TK is a Selectable Marker in Saccharomyces.

Figure 2:
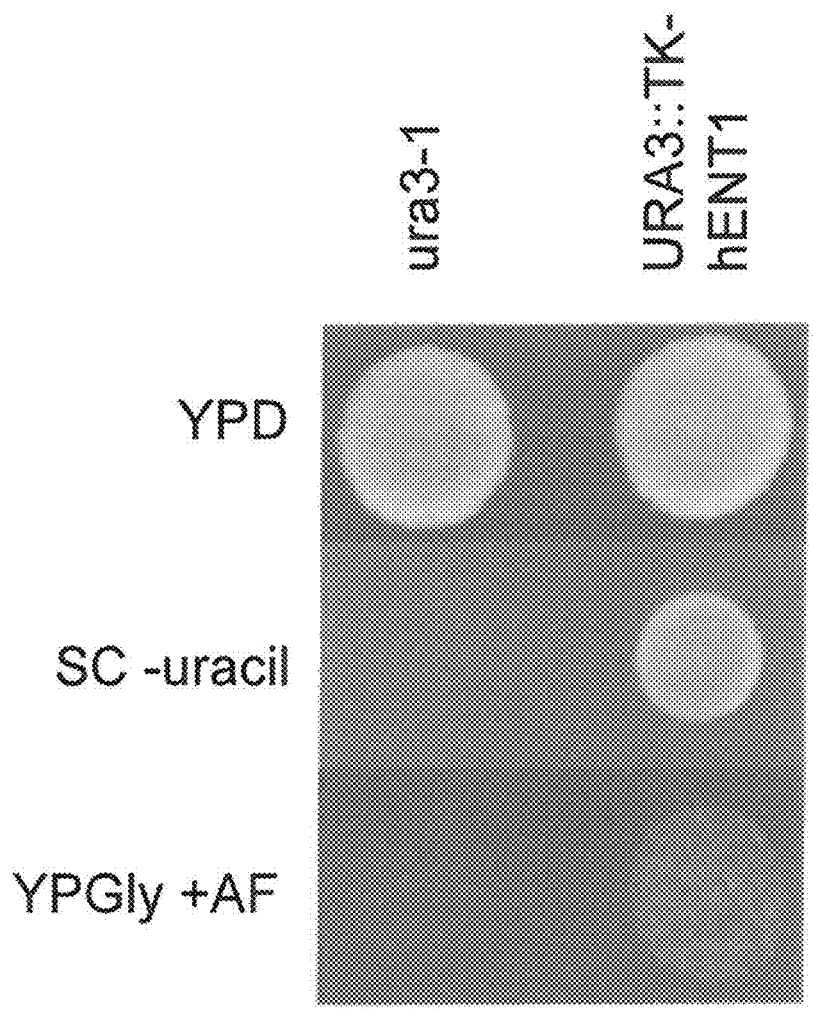
FIG. 2 is a set of photographs showing that antifolate drags can select for TK-hENT1 cells. Linearized p306-BrdU-Inc (1) was inserted into the ura3-1 locus of S. cerevisiae strain W303-1a (MATa leu2-3,112 trp1-1 can1-100 ura3-1 ade2-1 his3-11,15) (2) by transformation and selection on SC-uracil media. Antifolate drugs were lethal to the untransformed strain but had no effect on the resulting URA3 strain.
Figure 3:
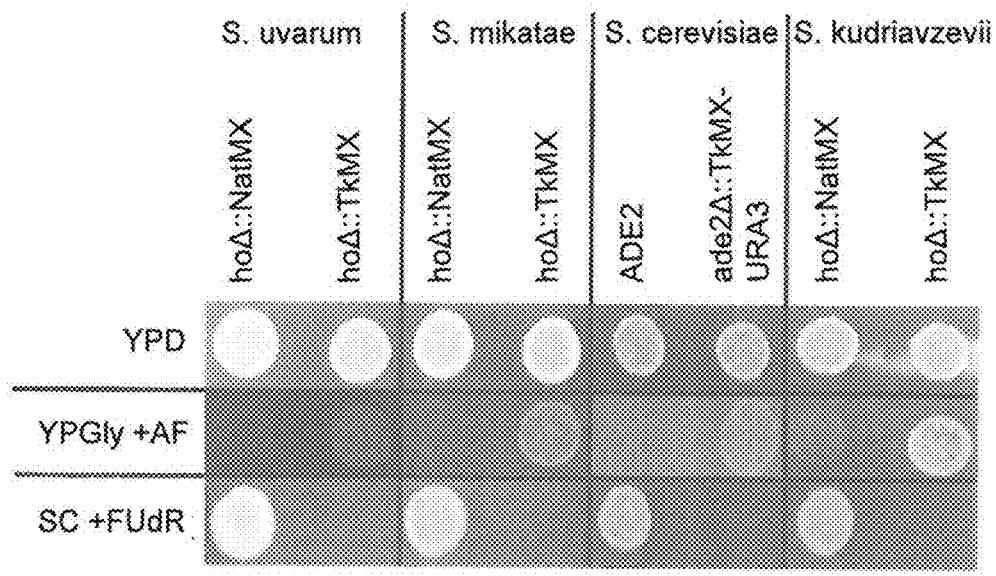
FIG. 3 is a set of photographs showing that TK cells can be differentiated from tk cells. Haploid strains of S. uvarum, S. mikatae, S. cerevisiae, and S. kudriavzevii were transformed with TkMX PCR product and selected on antifolate media. TkMX permitted growth on antifolate media and conveyed sensitivity to FUdR.

Human herpes simplex virus TK (HSV-TK) has been used previously in S. cerevisiae (along with the human nucleoside transporter hENT1) as a component in a reconstituted nucleotide salvage pathway (25) or to label newly-synthesized DNA with brominated nucleotides (26), but its use as a selectable marker has not been evaluated previously. First, we sought to devise a media formulation that could differentiate between TK and tk cells. Previous work demonstrated that cells unable to synthesize thymidine de novo due to a mutation in the thymidylate synthase gene CDC21 (also referred to as TMP1) could be rescued by the expression of TK and on media containing thymidine, although a high proportion of cells recovered after this treatment exhibited defective mitochondrial genomes (termed petite, or $\rho^-$ cells) (Sclafani and Fangman Genetics (1986) 114(3): 753-767). Certain antifolate drugs are able to reversibly inhibit thymidylate synthase in yeast, and they have been used in nucleotide salvage and labeling studies to eliminate native thymidine synthesis (25-27), which is known to be lethal if cells cannot escape this thymineless death (28). We found that an antifolate cocktail of methotrexate and sulfanilamide in YPD supplemented with thymidine and hypoxanthine was lethal to a wild-type strain but supported growth of a TK-hENT1 strain. As expected, using this media to select for TK transformants resulted in a high proportion of petite colonies. Replacing glucose in the media with the non-fermentable carbon source glycerol (YPGly+AF) and the addition of a high level of thymidine allowed us to select for cells that retained functional mitochondrial genomes (FIG. 2). Once a selection medium had been formulated, we tested the ability of the HSV-TK gene alone to function as a marker. Even without hENT1, constitutively expressed TK proved an effective marker in ail four diverse species of Saccharomyces that we tested (FIG. 3).

TK is a Counterselectable Marker in Saccharomyces.

Figure 4:
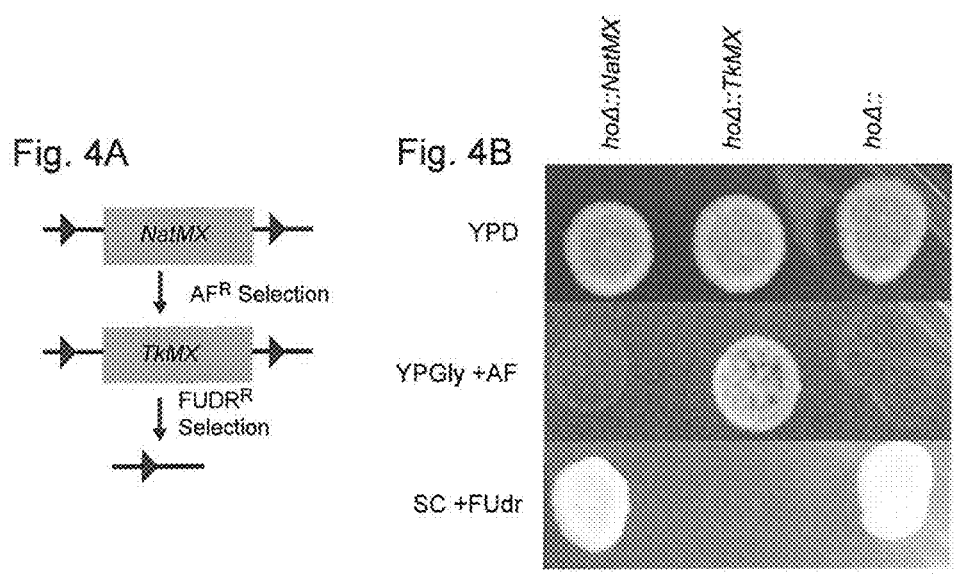
FIG. 4 is a set of figures showing that TkMX is a counterselectable marker across Saccharomyces.

With a stably integrated copy of HSV-TK in each of several genomes, we were able to evaluate counterselection media conditions. Various FUdR concentrations have been effectively used in other organisms (29-32), and we found that 50 µg/mL FUdR in synthetic complete (SC) media was sufficient to inhibit growth of the stably-integrated TK strains but allow growth of the tk wild-type cells (FIG. 3). As an initial test of our ability to recover newly generated tk wild-type cells, we transformed a strain of S. kudriavzevii that had regions of Identical sequence on either side of its hoΔ::NatMX locus with TkMX PCR product and selected for cells resistant to the antifolate drags (FIG. 4A), When counterselection with SC+FUdR media was conducted, only cells that had deleted the TkMX marker by homologous recombination survived and yielded colonies resistant to FUdR (FIG. 4B).

Counterselection relies on selection for the lack of gene activity in a cell, and thus, replacement of the counterselectable marker is phenotypically indistinguishable from a deactivating mutation in that marker or mutations in other genes that can cause drug resistance. For instance, null mutations in either URA3 or FUR4 are known to lead to spontaneous $FOA^R$ colonies (33), We compared the rate of spontaneous $FUdR^R$ and $FOA^R$ mutation by replacing the ADE2 coding sequence of RM11-1a (34) (a ura3 haploid strain of S. cerevisiae) with a TkMX-URA3 construct containing each gene under the control of its own promoter. After growth on non-selective media, only 1.7 times more FUdR$^R$ colonies arose than FOA$^R$ colonies, indicating that these counterselectable markers perform similarly.

The ultimate test of a selectable and counterselectable marker-based engineering scheme Is the ability to recover wild-type cells by the removal and subsequent replacement of the sequence of interest. Thus, we reinserted the native ADE2 sequence of our previously constructed ade2Δ::TkMX-URA3 strain by selecting for FUdR-resistance and compared the growth parameters of the ADE2 wild-type, ade2Δ::TkMX-URA3, and restored ade2Δ::ADE2 strains (FIG. 4C). The restored ade2Δ::ADE2 strains grew in an identical fashion to the wild-type ADE2 strain, indicating that they were unaffected by the insertion and replacement of TkMX. The ade2Δ::TkMX-URA3 strain exhibited a slower growth rate and lower final cell density than the other strains, most likely due to the deletion of ADE2.

A Double-Strand Break Generator and TK Enable Highly Efficient and Parallelized Genome Editing of Saccharomyces Strains.

To incorporate an inducible DSB feature, we fused a galactose-inducible SCEI endonuclease to the TkMX marker, forming HERP1.0 (Haploid Engineering and Replacement Protocol v1.0, FIG. 5A). We targeted HERP1.0 to the ADE2 gene of RM11-1a to evaluate its capability to enhance transformation. The ade2Δ::HERP1.0 strain was grown on galactose and transformed with S. uvarum ADE2 PCR product to eliminate the possibility of contamination by wild-type cells (FIG. 5B). The resulting transformation rates ranged from 0.17% to 0.86% of surviving cells, depending on the transformation method used (Table 3).

TABLE 3

Use of the HERP1.0 cassette results in high transformation rates. The ADE2 ORF was replaced with HERP1.0, then counterselected for with S. uvarum ADE2 sequence. Cells surviving the transformation procedure were determined by diluting the reaction 1000x, plating 1 μL onto YPD, and counting the colonies formed. The number of ADE2 insertions was determined similarly except 50 μL of diluted reaction was plated onto SC-adenine plates.

|  | LiAc/PEG-4000 80 min heat shock transformation | electroporation |
|---|---|---|
| # cells surviving | $8.4 \times 10^7$ | $5.5 \times 10^7$ |
| # ADE2$^+$ cells generated | $2.0 \times 10^5$ | $4.7 \times 10^5$ |
| transformation efficiency | 0.24% | 0.86% |

We wondered whether the high transformation rates enabled by the HERP cassette could allow for the direct investigation of pools of variants in parallel by the cotransformation of mixed PCR products into a population of cells. To assess the feasibility of this scheme, we amplified the ADE2 gene from all seven Saccharomyces species with primers that targeted them to the ADE2 locus in the S. cerevisiae ade2Δ::HERP1.0 strain (FIG. 5C), transformed the PCR products into galactose-induced cells, and then recovered and sequenced the ADE2 locus of each individual transformant. All seven ADE2 sequences were observed in the transformed cells (FIG. 5D).

Simultaneous Homozygous Genome Editing of Diploid Saccharomyces yeasts is Possible.

Figure 6:
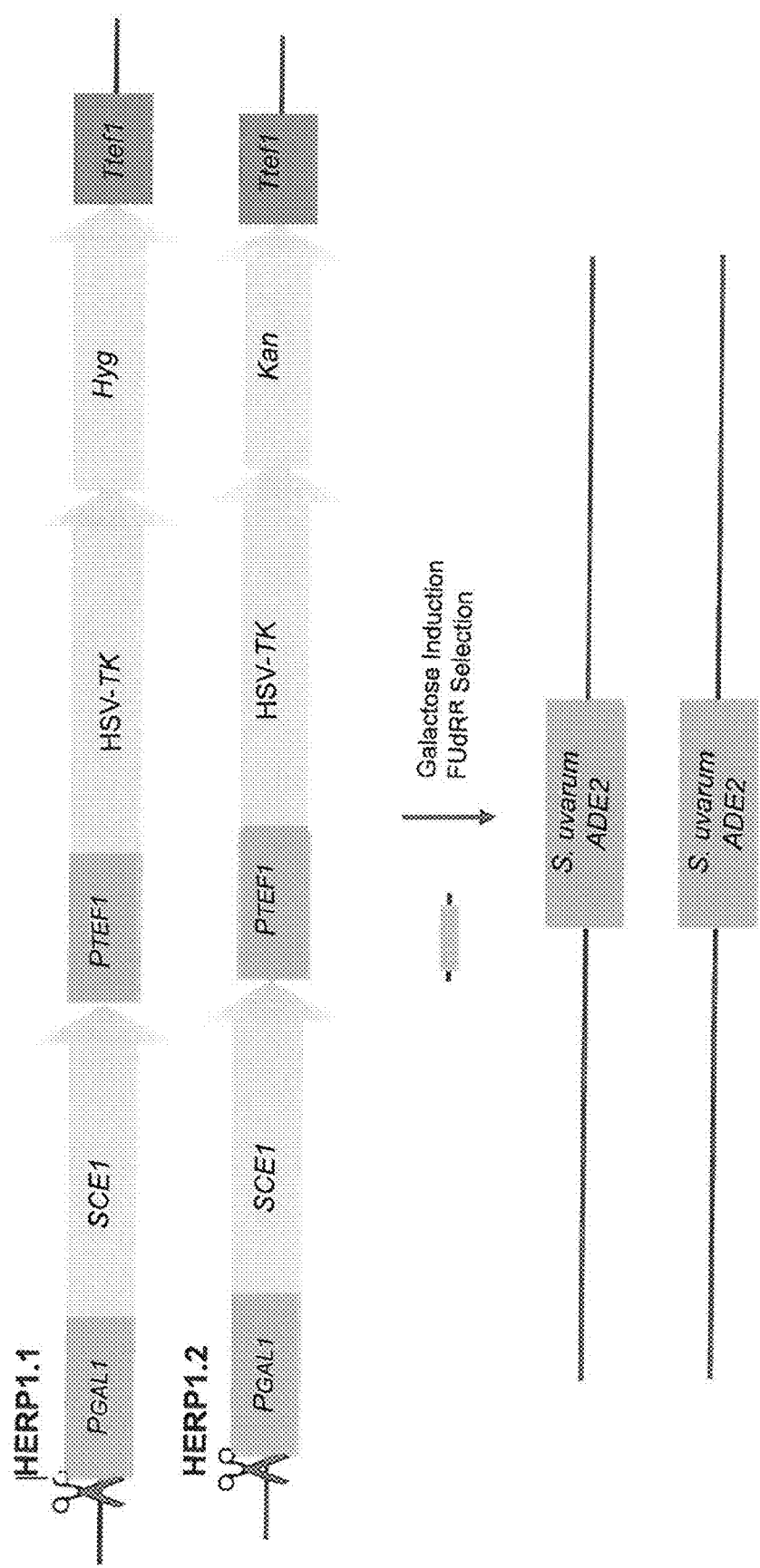
FIG. 6 is a schematic showing how HERP cassettes allow simultaneous replacement of both chromosomes in a diploid cell. Cells with two HERP cassettes at the same locus on homologous chromosomes replaced both with endogenous PCR products at a rate of ~$10^{-7}$ per surviving cell.

While most laboratory strains of Saccharomyces are stable haploids, almost all industrial and wild strains of Saccharomyces are not. Diploidy presents a barrier to using DSB-mediated transformation schemes because diploid cells prefer to repair DSBs using the homologous chromosome rather than exogenous linear DNA. This preference results in the minority of recovered strains (~4%) possessing the intended modification, even when a counterselectable marker is used (18). We hypothesized that a DSB generated simultaneously at the same locus on both chromosomes would prevent these undesired repair events. We created HERP cassettes that had the TK gene tagged with an 8× glycine linker and either a hygromycin-resistance (TK-Hyg) or G418-resistance (TK-Kan) gene, forming the HERP1.1 and HERP1.2 cassettes, respectively. These cassettes were used sequentially to delete both copies of ADE2 in M22, a wild S. cerevisiae strain isolated from a vineyard (35, 36). The resulting ade2Δ::HEKP1.1/ade2Δ::HERP1.2 strain was induced with galactose and transformed with a S. uvarum ADE2 PCR product designed to replace the inserted HERP cassettes (FIG. 6). Fifteen double replacement candidates were recovered from these plates, and 14 of the 15 candidates exhibited bands at the ADE2 locus consistent with the replacement of both HERP cassettes with the S. uvarum ADE2 PCR product.

To confirm this surprising result, eight of the double replacement candidates were sporulated, and their tetrads were dissected to separately examine the ADE2 allele present on each homologous chromosome. Three fully viable tetrads per candidate were examined by PCR and sequencing; all 96 spores possessed the S. uvarum ADE2 allele at their native ADE2 locus, indicating that all eight candidates were indeed homozygous for the inserted S. uvarum ADE2 sequence.

To determine whether this approach was generalizable to other Saccharomyces species, we repeated the procedure using S. uvarum, an early-diverging member of the genus. The HERP1.1 and HERP1.2 cassettes were inserted sequentially into chromosome 5 of the S. uvarum strain CBS 7001. The HERP cassettes were then replaced with a constitutively-expressed yEGFP construct (37). Eight candidates were obtained, and when screened, three exhibited a PCR product consistent with yEGFP replacement of both HERP cassettes. Sporulation and tetrad analysis confirmed that all three candidates were the product of double replacement events, yielding a recovery rate of $5.6 \times 10^{-7}$ double replacements per surviving cell, which was similar to the rate of $2.8 \times 10^{-7}$ in S. cerevisiae.

DERP

The DERP cassette will be constructed by gap repair in yeast (a process where a yeast cell assembles PCR fragments and a linearized yeast-replicatable plasmid into a desired construct). Specifically, the $P_{GAL4}$~SCEI, TK, Nat$^R$, and Hyg$^R$ fragments will be PCR amplified from plasmids containing those sequences with primers that attach ~40-bp of sequence on either end of a fragment that directs the yeast cell to connect it to fragments as intended. These fragments are repaired by the yeast cell into the aforementioned plasmid, which is then able to be propagated into newly-divided yeast cells and is recoverable into E. coli by electroporation. See FIG. 8.

HERP2.0.1

In an effort to enhance the efficiency of HERP2.0.1, a nuclear localization signal (MLS) was attached to the 5' end of the SCEI sequence via gap repair in yeast. Because induction by the Tet-ON system generally results in lower overall protein production, the NLS should concentrate the ScEI protein inside the nucleus thus increasing its cutting action at its recognition site and increasing the efficiency of the system.

Supplementary Protocol Exemplifying One Embodiment of the Invention

The purpose of this document is to provide you with an easy-to-follow guide to using the HERP cassettes, We will go through the preparation of the selection and counterselection media, the catering and transformation for insertion of the HERP cassettes, and counterselection replacement of the HERP cassettes.

A. Preparing Media: Yeast Extract-Peptone-Glycerol+Amifolates (YPGly+AF)

1) Add the following components to a 2-L Erlenmeyer flask
10 g yeast extract
20 g peptone
5 g sulfanilamide
50 hypoxanthine
18 g agar
900 mL ddH$_2$O
Mix to dissolve as much as possible (agar and sulfanilamide won't dissolve until heated).

2) Autoclave for no more than 20 minutes on a liquid cycle.

3) Once autoclaved, cool to 50° in a water bath, then add the following and mix:
5 g thymidine
200 mg methotrexate
100 ml 50% (v/v) glycerol, sterilized
(NOTA BENE: the standard operating procedure for adding compounds after autoclaving is to dissolve them in a solvent, filter, then add to the media; this generally is difficult or impossible for methotrexate and thymidine due to the amount required. For the last two years, I've been adding the solid chemicals directly to the cooled media, and I've never had contamination. I suspect that the extreme conditions prevent microbial growth. Also, both methotrexate and thymidine are sensitive to heat, so take care to not add them early.)

4) Pour ~20 mL into plastic petri dishes and allow to set. You have now made YPGly+AF media.

B. Preparing Media: Synthetic Complete+S-fluorodeoxyuridine (SC+FUdR)

1) In a 2-L Erlenmeyer flask, make 1 L of Synthetic Complete agar using your favorite provider's formulation. Autoclave then cool to 50° in a water bath.

2) Dissolve 55 mg of FUdR into 1.1 mL of ddH2O, filter sterilize, then add 1 mL of FUdR solution to cooled SC agar and mix.

3) Poor ~20 ml into plastic petri dishes and allow to set. You nave now made SC+FUdR agar.
(NB: an alternate method to make SC+FUdR plates is to make a 1000× stock solution of 50 mg/mL FUdR in water, filter, then spread enough concentrate onto the surface of a premade SC plate to bring the final concentration to 50 μg/mL (20 μL of concentrate mixed with 80 μL of water, then spread onto the surface of a plate contains 20 mL of SC agar))

C. Inserting the HERP Cassettes.

1) Design Primers with Overhangs that Target the Cassette to your Desired Locus.

a) The 5' overhangs dictate where the cassette will be integrated, and the length needed depends on the species you're manipulating (40 bp for *S. cerevisiae, S. paradoxus, S. uvarum, & S. eubayanus,* 50 bp for *S. mikatae,* and 70 for *S. kudriavzevii; S. arbaricola*'s length requirement is unknown). The longer these overhangs are the more efficient integration will be, although longer overhangs usually mean longer oligonucleotides, which are expensive and sometimes difficult to use.

b) The 3' ends amplify the cassette from either the primer or yeast genomic DNA. While we have constructed both plasmids and stably-integrated yeast strains with all three HERP cassettes, the yeast strains provide an advantage over the plasmid constructs. HERP cassettes with an adjacent I-SceI recognition site are unstable in bacteria, result of in the plasmid new being recovered. In yeast, SCE2 is actively repressed while growing on glucose which prevents leaky nuclease expression. Because of this active repression, the yeast strains tolerate an I-SceI site adjacent to the HERP cassettes, which in turn reduces the length of oligonucleotide needed to provide both a priming site and a targeting overhang. The authors strongly recommend using the yeast strains as PCR templates for HERP cassette amplification. If the plasmids are used, then the 18-bp I-SceI sequence must be included on the oligo between the S' amplification sequence and the 5' targeting overhang (Table S5).

2) Amplify the HERP cassette of choice using your targeting primers and a high-fidelity polymerase such as New England Biolab's Phusion system. If your reaction makes use of DMSO or other harsh chemicals, clean your PCR product with a column before proceeding.

3) Culture your strain of choice by innoculating 50 ml of YPD media with enough overnight capture of your strain to bring the OD$_{800}$ to 0.2-0.25. Shake at the optimal temperature for your strain or species until the culture's OD$_{800}$ reaches 0.85-1.0.

4) Harvest the cells by centrifugation in a 50-mL conical vial at 3000 RPM for 5 minutes. Remove supernatant, wash with 25 mL water, and spin at 3000 RPM for 5 minutes. Remove supernatant and suspend cells in 1 mL of water.

5) Aliquot 100 μL cell suspension to microcentrifuge tubes, spin for 30 seconds at max speed in a microcentrifuge, and remove supernatant.

6) Add the following reagents to each cell pellet IN ORDER:
240 μL 50% polyethylene glycol, average MW 4000, filter sterilized
36 μL 1 M lithium acetate, filter sterilized
5 μL 20 mg/mL boiled sonicated salmon sperm DNA
79 μL HERP cassette PCR product or water (for control)

7) Suspend Cell Pellet in Transformation Mixture and Beat Shock.
(NB: for optimal transformation efficiency you must empirically determine what time, temperature, and/or additive conditions give the most transformants for your species or strain. Our suggestion is to use a yeast replicating plasmid with a dominant drug marker and evaluate a number of conditions as in Gietz & Woods, 2002. In general, 30 minute heat shocks at 42° works well for *S. cerevisiae,* while the psychrophillic species generally only tolerate heat shocks of 37° (*S. kudriavzevii* only tolerate 34°. *S. mikatae* doesn't tolerate the transformation reaction conditions well, and requires a room temperature incubation of 10 minutes followed by a 37° shock for 5 minutes.)

8) Once heat-shocking has been completed, spin the reactions for 30 seconds at max speed, remove the supernatant, and suspend the cells in 600 μL of YPD. Transfer to glass culture tubes and spin in a culture wheel for 3 hours at the strain's or species' optimal temperature.

9) Spread 200 μL of recovered cells to each of three YPGly+AF plates. Only one 200 μl volume of control reaction, however, needs to be plated. Once all the liquid has been absorbed, store agar up at the optimal temperature. Colonies will appear in 3-10 days.

10) Streak colonies out to fresh YPGly+AF plates. Analyze by amplifying target locus via PCR and/or sequencing across the insertion junction.

D. Counterselective Replacement of the HERP Cassette

1) Once you have molecularly confirmed the insertion of the HERP cassette, phenotypically confirm its sensitivity to FUdR by spotting ~1,000 cells onto SC+FUdR plates multiple times. Sensitive strains should exhibit no growth, while insensitive strains will rapidly grow.

2) Once your HERP insertion is confirmed and you have established FUdR sensitivity, begin by inoculating the strain in 50 mL of 2×YPA$^{100}$+4% galactose (see main text) to an OD600 of 0.2-0.25 and culture at the optimal temperature.

3) Once an OD600 of 0.85-1.0 is reached, repeat steps C4 to C6, except replace the HERP cassette PCR product in C6 with your desired replacement PCR product.

4) Once the heat shock is completed, remove the supernatant, suspend in 600 μL water, and spread 200 μL onto each of three SC plates. Incubate at optimal temperature for 24 hours.

5) After 24 hours, incubate plates at 4° for one hour then lightly replicate plates to SC+FUdR plates. Re-replicate to fresh FUdR plates no more than once a day to reduce background growth. Colonies will appear in 2-5 days, longer if glucose is replaced by glycerol.

TABLE 53

Illustration of oligonucleotide design for HERP cassette insertion

| Primer Name | Primer Sequence | DNA template |
|---|---|---|
| HERP Forward Primer For Plasmid Template Amplification | (YFG targeting sequence)-TAGGGATAACAGGGTAATGTCGACTTGGATGGACGC | plasmid |
| HERP Reverse Primer For Plasmid or gDNA Amplification | (YFG targeting sequence)-GAGCTCGTTTTCGACACTGGATGGCG | plasmid or gDNA |
| HERP Forward Primer For gDNA Template Amplification | (YFG targeting sequence)-*TAGGGATAACAGGGTAATTTGG* | gDNA |

Using HERP plasmids as PCR templates requires the addition of the I-SceI recognition site (italics) inserted between the 3' amplification sequence (bold) and the 5' sequence that targets the cassette to Your Favorite Gene (YFG), resulting in longer oligonucleotides. When gDNA of strains possessing an integrated HERP cassette is used as a PCR template, however, the I-SceI sequence is included within the 3' amplification sequence (italic bold), reducing the overall length of the oligonucleotide required.

REFERENCES FROM MATERIALS AND METHODS FOR HERP CONSTRUCTION

1. Viggiani C J, Aparicio O M (2006) New vectors for simplified construction of BrdU-Incorporating strains of *Saccharomyces cerevisiae. Yeast* 23:1045-1051.
2. Veal E A, Ross S J, Malakasi P, Peacock E, Morgan B A (2003) Ybp1 is required for the hydrogen peroxide-induced oxidation of the Yap1 transcription factor. *J Biol Chem* 278:30896-904.
3. Scannell D R. et al. (2011) The awesome power of yeast evolutionary genetics: new genome sequences and strain resources for the *Saccharomyces* sensu stricto genus, G3 *Genes|Genomes|Genetics* 1:11-25.
4. Hittinger C T et al. (2010) Remarkably ancient balanced polymorphisms in a multi-locus gene network. *Nature* 464:54-8.
5. Storici F, Resnick M A (2006) The Delitto Perfetto approach to in vivo site-directed mutagenesis and chromosome rearrangements with synthetic oligonucleotides in yeast. *Methods Enzymol* 409:329-45.
6. Sikorski R S, Hieter P (1989) A system of shuttle vectors and yeast host strains designed for efficient manipulation of DNA in *Saccharomyces cerevisiae. Genetics* 122:19-27.
7. Hittinger C T, Carroll S B (2007) Gene duplication and the adaptive evolution of a classic genetic switch. *Nature* 449:677-81.
8. Yanisch-Perron C, Vieira J, Messing J (1985) Improved M13 phage cloning vectors and host strains: nucleotide sequences of the M13mp18 and pUC19 vectors. *Gene* 33:103-19.
9. Goldstein A L, McCusker J H (1999) Three new dominant drug resistance cassettes for gene disruption in. *Saccharomyces cerevisiae. Yeast* 15:1541-53.
10. Güldener U, Heck S, Fielder T, Beinhauer J, Hegemann J H (1996) A new efficient gene disruption cassette for repeated use in budding yeast. *Nucleic Acids Res* 24:2519-24.
11. Altschul S F, Gish W, Miller W, Myers E W, Lipman D J (1990) Basic local alignment search tool. *J Mol Biol* 215:403-10.
12. Kearse M et al. (2012) Geneious Basic: an integrated and extendable desktop software platform for the organization and analysis of sequence data. *Bioinformatics* 28:1647-9.

REFERENCES FROM DESCRIPTION

1. Gratz S J et al. (2013) Genome Engineering of *Drosophila* with the CRISPR RNA-guided Cas9 Nuclease. *Genetics* 194:1029-35.
2. Tzur Y B et al. (2013) Heritable custom genomic modifications in *Caenorhabditis elegans* via a CRISPR-Cas9 system. *Genetics* 195:1181-5.
3. Jiang W et al. (2013) Demonstration of CRISPR/Cas9/sgRNA-mediated targeted gene modification in *Arabidopsis*, tobacco, sorghum and rice. *Nucleic Acids Res* 41:e188.
4. Hwang W Y et al. (2013) Efficient genome editing in zebrafish using a CRISPR-Cas system. *Nat Biotechnol* 31:227-9.
5. Scannell D R et al. (2011) The awesome power of yeast evolutionary genetics: new genome sequences and strain resources for the *Saccharomyces* sensu stricto genus, G3 1:11-25.

6. Libkind D et al. (2011) Microbe domestication and the identification of the wild genetic stock of lager-brewing yeast. *Proc Natl Acad Sci USA* 108:14539-44.
7. Wang S-A, Bai F-Y (2008) *Saccharomyces arboricolus* sp. nov., a yeast species from tree bark. *Int J Syst Evol Microbiol* 58:510-4.
8. Lodolo E J, Kock J L F, Axcell B C, Brooks M (2008) The yeast *Saccharomyces cerevisiae*—the main character in beer brewing. *FEMS Yeast Res* 8:1018-36.
9. Steen E J et al. (2008) Metabolic engineering of *Saccharomyces cerevisiae* for the production of n-butanol. *Microb Cell Fact* 7:36.
10. Matsushika A, Inoue H, Kodaki T, Sawayama S (2009) Ethanol production from xylose in engineered *Saccharomyces cerevisiae* strains: current state and perspectives. *Appl Microbiol Biotechnol* 84:37-53.
11. Peris D, Lopes C A, Belloch C, Querol A, Barrio E (2012) Comparative genomics among *Saccharomyces cerevisiae*×*Saccharomyces kudriavzevii* natural hybrid strains isolated from wine and beer reveals different origins. *BMC Genomics* 13:407.
12. Botstein D, Fink G R (2011) Yeast: an experimental organism for 21 st century biology. *Genetics* 189:695-704.
13. Hittinger C T (2013) *Saccharomyces* diversity and evolution: a budding model genus. *Trends Genet* 29:309-17.
14. Boeke J D, LaCroute F, Fink G R (1984) A positive selection for mutants lacking orotidine-5'-phosphate decarboxylase activity in yeast: 5-fluoro-orotic acid resistance. *Mol Gen Genet* 197:345-346.
15. Glover L, Horn D (2009) Site-specific QUA double-strand breaks greatly increase stable transformation efficiency in *Trypanosoma brucei*. *Mol Biochem Parasitol* 166:194-7.
16. Choulika A, Perrin A, Dujon B, Nicolas J F {1995} Induction of homologous recombination in mammalian chromosomes by using the I-SceI system of *Saccharomyces cerevisiae*. *Mol Cell Biol* 15:1968-73.
17. Storici F, Durham C L, Gordenin D a, Resnick M a (2003) Chromosomal site-specific double-strand breaks are efficiently targeted for repair by oligonucleotides in yeast *Proc Natl Acad Sci USA* 100:14994-9.
18. Stories F, Resnick M A (2006) The Delitto Perfetto approach to in vivo site-directed mutagenesis and chromosome rearrangements with synthetic oligonucleotides in yeast. *Methods Enzymol* 409:329-45.
19. Stuckey S, Storici F (2013) Gene knockouts, in vivo site-directed mutagenesis and other modifications using the Delitto Perfetto system in *Saccharomyces cerevisiae*. *Methods Enzymol* 533:103-31.
20. Mülleder M et al. (2012) A prototrophic deletion mutant collection for yeast metabolomics and systems biology. *Nat Biotechnol* 30:1176-8.
21. Vandersluis B et al. (2014) Broad metabolic sensitivity profiling of a prototrophic yeast deletion collection. *Genome Biol* 15:R64.
22. Weissman S M, Smellie R M S, Paul J (1960) Studies on the biosynthesis of deoxyribonucleic acid by extracts of mammalian cells IV. The phosphorylation of thymidine. *Biochim Biophys Acta* 45:101-110.
23. Grivell A R, Jackson J F (1968) Thymidine kinase: evidence for its absence from: *Neurospora crassa* and some other micro-organisms, and the relevance of this to the specific labelling of deoxyribonucleic acid. *J Gen Microbiol* 54:307-17.
24. Duraisingh M T, Triglia T, Cowman A F (2002) Negative selection of *Plasmodium falciparum* reveals targeted gene deletion by double crossover recombination. *Int J Parasitol* 32:81-9.
25. Vernis L, Piskur J, Diffley J F X (2003) Reconstitution of an efficient thymidine salvage pathway in *Saccharomyces cerevisiae*. *Nucleic Acids Res* 31:1-7.
26. Viggiani C J, Aparicio O M (2006) New vectors for simplified construction of BrdU-Incorporating strains of *Saccharomyces cerevisiae*. *Yeast* 23:1045-1051.
27. Wickner R B (1974) Mutants of *Saccharomyces cerevisiae* that incorporate deoxythymidine-5'-monophosphate into deoxyribonucleic acid in vivo. *J Bacteriol* 117:252-60.
28. Ahmad S I, Kirk S H, Eisenstark a (1998) Thymine metabolism and thymineiess death in prokaryotes and eukaryotes. *Annu Rev Microbiol* 52:591-625.
29. Sachs M S et al. (1997) Expression of herpes virus thymidine kinase in *Neurospora crassa*. *Nucleic Acids Res* 25:2389-95.
30. Krappmann S, Bayram Ö, Braus G H (2005) Deletion and Allelic Exchange of the *Aspergillus fumigatus* veA Locus via a Novel Recyclable Marker Module, *Eukaryot Cell* 4.
31. Hodson J A. Bailis J M, Forsburg S L (2003) Efficient labeling of fission yeast *Schizosaccharomyces pombe* with thymidine and BUdR. *Nucleic Acids Res* 31:134e-134.
32. Khang C H, Park S-Y, Lee Y-H, Kang S (2005) A dual selection based, targeted gene replacement tool for *Magnaporthe grisea* and *Fusarium oxysporum*. *Fungal Genet Biol* 42:483-92.
33. Jund R, Weber E, Chevallier M-RC (1988) Primary structure of the uracil transport protein of *Saccharomyces cerevisiae*. *Eur J Biochem* 171:417-24.
34. Brem R, Yvert G, Clinton R, Kruglyak L (2002) Genetic dissection of transcriptional regulation in budding yeast. *Science* (80-) 296:752-5.
35. Mortimer R K (2000) Evolution and Variation of the Yeast (*Saccharomyces*) Genome. *Genome Res* 10:403-409.
36. Fay J C, McCullough H L, Sniegowski P D, Eisen M B (2004) Population genetic variation in gene expression is associated with phenotypic variation in *Saccharomyces cerevisiae*. *Genome Biol* 5:R26.
37. Hittinger C T, Carroll S B (2007) Gene duplication and the adaptive evolution of a classic genetic switch. *Nature* 449:677-81.
38. Pratt R J, Aramayo R (2002) Improving the efficiency of gene replacements in *Neurospora crassa*: a first step towards a large-scale functional genomics project. *Fungal Genet Biol* 37:56-71.
39. Araya C L, Fowler D M (2011) Deep mutational scanning: assessing protein function on a massive scale. *Trends Biotechnol* 29:435-42.
40. Mali P et al. (2013) RNA-guided human genome engineering via Cas9. *Science* 339:823-6.
41. Cong L et al, (2013) Multiplex genome engineering using CRISPR/Cas systems. *Science* 339:819-23.
42. Cradick T J, Fine E J, Antico C J, Bao G (2013) CRISPR/Cas9 systems targeting β-globin and CCR5 genes have substantial off-target activity. *Nucleic Acids Res* 41:9584-92.
43. Haurwitz R E, Jinek M, Wiedenheft B, Zhou K, Doudna J A (2010) Sequence- and structure-specific RNA processing by a CRISPR endonuclease. *Science* 329:1355-8.

44. Gao Y, Zhao Y (2014) Self-processing of ribozyme-flanked RNAs into guide RNAs in vitro and in vivo for CRISPR-mediated genome editing. *J Integr Plant Biol* 56:343-9.
45. DiCarlo J E et al. (2013) Genome engineering in *Saccharomyces cerevisiae* using CRISPR-Cas systems. *Nucleic Acids Res* 41:4336-43.
46. Hittinger C T, Rokas A, Carroll S B (2004) Parallel inactivation of multiple GAL pathway genes and ecological diversification in yeasts. *Proc Natl Acad Sci USA* 101:14144-9.
47. Hittinger C T et al. (2010) Remarkably ancient balanced polymorphisms in a multi-locus gene network. *Nature* 464:54-8.
48. Martchenko M, Levitin A, Hogues H, Nantel A, Whiteway M (2007) Transcriptional rewiring of fungal galactose-metabolism circuitry. *Curr Biol* 17:1007-13.
49. Young M J, Court D A (2008) Effects of the S288c genetic background and common auxotrophic markers on mitochondrial DNA function in *Saccharomyces cerevisiae*. *Yeast* 25:903-12.
50. Belli G, Gari E, Piedrafita L, Aldea M, Herrero E (1998) An activator/represser dual system allows tight tetracycline-regulated gene expression in budding yeast. *Nucleic Acids Res* 26:942-7.
51. Gietz R D, Woods R a (2002) Transformation of yeast by lithium acetate/single-stranded carrier DNA/polyethylene glycol method. *Methods Enzymol* 350:87-96.
52. Thompson J R, Register E, Curotto J, Kurtz M, Kelly R (1998) An improved protocol for the preparation of yeast cells for transformation by electroporation. *Yeast* 14:565-71.

We claim:

1. A method of genome editing, allele replacement or genetic engineering of a fungus or protist, the method comprising:
   generating or obtaining a construct, the construct comprising a first polynucleotide encoding a thymidine kinase operably connected to a first promoter; a second polynucleotide encoding an endonuclease operably connected to a second promoter;
   and a third polynucleotide comprising a recognition site for the endonuclease, wherein the second promoter is an inducible promoter;
   introducing the construct into the fungus or protist cells; and
   selecting for thymidine kinase by growing the fungus or protists on antifolate containing medium.

2. The method of claim 1, wherein the construct further comprises a fourth polynucleotide encoding at least one selectable marker.

3. The method of claim 2, wherein the selectable marker confers resistance to at least one of hygromycin, kanamycin, zeocin, phleomycin or nourceothricin.

4. The method of claim 1, wherein the construct further comprises 20 to 2000 nucleotides homologous to the fungi or protists.

5. The method of claim 1, wherein the thymidine kinase is a Herpes Simplex Virus thymidine kinase.

6. The method of claim 1, wherein the first promoter is a constitutive promoter functional in fungi or protists.

7. The method of claim 1, wherein the second promoter is selected from the group consisting of the GAL1 promoter, the Tet-On system and beta-estradiol.

8. The method of claim 1, wherein the endonuclease is selected from the group consisting of SceI, I-CreI, I-CeuI, I-MsoI, I-DmoI, I-SceII-VII, I-ChuI and CRISPR/Cas9.

9. The method of claim 1, wherein a tetracycline responsive activator is fused to the first polynucleotide.

10. The method of claim 1, further comprising assaying for integration of the construct into the chromosome of the cells.

11. The method of claim 1, further comprising inducing the fungus or protist cells to produce the endonuclease; and selecting the cells in the presence of an agent that becomes toxic in the presence of thymidine kinase.

12. The method of claim 1, wherein the antifolate containing medium comprises thymidine and methotrexate and/or sulfanilamide.

13. The method of claim 1, wherein the carbon source in the antifolate containing medium is glycerol or another non-fermentable carbon source.

14. The method of claim 11, wherein the agent is 5'fluorodeoxyuridine (FUdR).

15. The method of claim 11, further comprising assaying the selected cells for the loss of thymidine kinase.

16. The method of claim 1, wherein the construct further comprises a target polynucleotide for insertion into the genome of the fungi or protist.

17. The method of claim 16, wherein more than one construct each comprising a different target polynucleotide are incorporated into more than one fungus or protist cells.

18. The method of claim 17, wherein the fungi or protist cells are diploid.

19. The method of claim 18, wherein at least two constructs are introduced into the fungus or protist cells and the at least two constructs each have a different selectable marker and further comprising selecting the cells for the selectable markers.

20. The method of claim 1, wherein the fungi are *Saccharomyces* or *Neurospora*.

* * * * *

SEQUENCE LISTING

```
<160> NUMBER OF SEQ ID NOS: 71

<210> SEQ ID NO 1
<211> LENGTH: 18
<212> TYPE: DNA
<213> ORGANISM: Artificial Sequence
<220> FEATURE:
<223> OTHER INFORMATION: Synthetic meganucleases

<400> SEQUENCE: 1
tagggataac agggtaat                                                  18

<210> SEQ ID NO 2
<211> LENGTH: 18
<212> TYPE: DNA
<213> ORGANISM: Artificial Sequence
<220> FEATURE:
<223> OTHER INFORMATION: Synthetic meganucleases

<400> SEQUENCE: 2
attaccctgt tatccca                                                   18

<210> SEQ ID NO 3
<211> LENGTH: 22
<212> TYPE: DNA
<213> ORGANISM: Artificial Sequence
<220> FEATURE:
<223> OTHER INFORMATION: Synthetic meganucleases

<400> SEQUENCE: 3
caaaacgtcg tgagacagtt tg                                             22

<210> SEQ ID NO 4
<211> LENGTH: 22
<212> TYPE: DNA
<213> ORGANISM: Artificial Sequence
<220> FEATURE:
<223> OTHER INFORMATION: Synthetic meganucleases

<400> SEQUENCE: 4
caaactgtct cacgacgttt tg                                             22

<210> SEQ ID NO 5
<211> LENGTH: 27
<212> TYPE: DNA
<213> ORGANISM: Artificial Sequence
<220> FEATURE:
<223> OTHER INFORMATION: Synthetic meganucleases
```

<400> SEQUENCE: 5
taactataac ggtcctaagg tagcgaa					27

<210> SEQ ID NO 6
<211> LENGTH: 27
<212> TYPE: DNA
<213> ORGANISM: Artificial Sequence
<220> FEATURE:
<223> OTHER INFORMATION: Synthetic meganucleases

<400> SEQUENCE: 6
ttcgctacct taggaccgtt atagtta					27

<210> SEQ ID NO 7
<211> LENGTH: 60
<212> TYPE: DNA
<213> ORGANISM: Artificial Sequence
<220> FEATURE:
<223> OTHER INFORMATION: Synthetic primer: TkMX F WGA

<400> SEQUENCE: 7
ctaggataca gttctcacat cacatccgaa cataaacaac catggcttcg tacccctgcc					60

<210> SEQ ID NO 8
<211> LENGTH: 60
<212> TYPE: DNA
<213> ORGANISM: Artificial Sequence
<220> FEATURE:
<223> OTHER INFORMATION: Synthetic primer: TkMX R WGA

<400> SEQUENCE: 8
agttcttgaa aacaagaatc tttttattgt cagtactgat cagttagcct cccccatctc					60

<210> SEQ ID NO 9
<211> LENGTH: 25
<212> TYPE: DNA
<213> ORGANISM: Artificial Sequence
<220> FEATURE:
<223> OTHER INFORMATION: Synthetic primer: Suva-HO:-843F WGA

<400> SEQUENCE: 9
tgtaaattca cacacgagtg tcacg					25

<210> SEQ ID NO 10
<211> LENGTH: 30
<212> TYPE: DNA
<213> ORGANISM: Artificial Sequence
<220> FEATURE:
<223> OTHER INFORMATION: Synthetic primer: Suva-HO:+2011R WGA

<400> SEQUENCE: 10 aaaactttt gtttgcattc aattatatcg					30

<210> SEQ ID NO 11
<211> LENGTH: 59
<212> TYPE: DNA
<213> ORGANISM: Artificial Sequence
<220> FEATURE:
<223> OTHER INFORMATION: Synthetic primer: pDERP::I-SceI R WGA

<400> SEQUENCE: 11
cgaggcaagc taaacagatc tctagaccta ttatttcagg aaagtttcgg aggagatag					59

<210> SEQ ID NO 12
<211> LENGTH: 59

```
<212> TYPE: DNA
<213> ORGANISM: Artificial Sequence
<220> FEATURE:
<223> OTHER INFORMATION: Synthetic primer: pDERP::TEF F WGA

<400> SEQUENCE: 12
ctatctcctc cgaaactttc ctgaaataat aggtctagag atctgtttag cttgcctcg      59

<210> SEQ ID NO 13
<211> LENGTH: 60
<212> TYPE: DNA
<213> ORGANISM: Artificial Sequence
<220> FEATURE:
<223> OTHER INFORMATION: Synthetic primer: pDERP::hyg frag 1 F WGA

<400> SEQUENCE: 13 agatgggggea ggctaacgga ggtggaggtg gaggtggagg tatgggtaaa aagcctgaac    60

<210> SEQ ID NO 14
<211> LENGTH: 59
<212> TYPE: DNA
<213> ORGANISM: Artificial Sequence
<220> FEATURE:
<223> OTHER INFORMATION: Synthetic primer: pTKKanMX::Kan F WGA

<400> SEQUENCE: 14
gagatggggg aggctaacgg aggtggaggt ggaggtggag gtatgggtaa ggaaaagac     59

<210> SEQ ID NO 15
<211> LENGTH: 60
<212> TYPE: DNA
<213> ORGANISM: Artificial Sequence
<220> FEATURE:
<223> OTHER INFORMATION: Synthetic primer: pDERP::TEF R WGA

<400> SEQUENCE: 15
cagctcccgg agacggtcac agcttgtctg taagcggatg gagctcgttt tcgacactgg    60

<210> SEQ ID NO 16
<211> LENGTH: 60
<212> TYPE: DNA
<213> ORGANISM: Artificial Sequence
<220> FEATURE:
<223> OTHER INFORMATION: Synthetic primer: pUC19::TkMX F #2

<400> SEQUENCE: 16
cagtcacgac gttgtaaaac gacggccagt gaattcagat ctgtttagct tgccttgtcc    60

<210> SEQ ID NO 17
<211> LENGTH: 60
<212> TYPE: DNA
<213> ORGANISM: Artificial Sequence
<220> FEATURE:
<223> OTHER INFORMATION: Synthetic primer: pUC19::TkMX R #2

<400> SEQUENCE: 17
ggtcgactct agaggatccc cgggtaccga gctcgaattc gagctcgttt tcgacactgg    60

<210> SEQ ID NO 18
<211> LENGTH: 60
<212> TYPE: DNA
<213> ORGANISM: Artificial Sequence
<220> FEATURE:
<223> OTHER INFORMATION: Synthetic primer: TK-URA3 F

<400> SEQUENCE: 18
```
cgccgccatc cagtgtcgaa aacgagctcg attcggtaat ctccgaacag aaggaagaac    60

<210> SEQ ID NO 19
<211> LENGTH: 60
<212> TYPE: DNA
<213> ORGANISM: Artificial Sequence
<220> FEATURE:
<223> OTHER INFORMATION: Synthetic primer: TK-URA3 R

<400> SEQUENCE: 19
gttcttcctt ctgttcggag attaccgaat cgagctcgtt ttcgacactg gatggcggcg    60

<210> SEQ ID NO 20
<211> LENGTH: 20
<212> TYPE: DNA
<213> ORGANISM: Artificial Sequence
<220> FEATURE:
<223> OTHER INFORMATION: Synthetic primer: MX marker swap F WGA

<400> SEQUENCE: 20
aaacgctccc ctcacagacg    20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer: MX marker swap R WGA

<400> SEQUENCE: 21
ctgggcagat gatgtcgagg    20

<210> SEQ ID NO 22
<211> LENGTH: 60
<212> TYPE: DNA
<213> ORGANISM: Artificial Sequence
<220> FEATURE:
<223> OTHER INFORMATION: Synthetic primer: pHERP-Gal::Pgal1 F WGA

<400> SEQUENCE: 22
ttacccaact taatcgcctt gcagcacatc ccccttgga tggacgcaaa gaagtttaat    60

<210> SEQ ID NO 23
<211> LENGTH: 22
<212> TYPE: DNA
<213> ORGANISM: Artificial Sequence
<220> FEATURE:
<223> OTHER INFORMATION: Synthetic primer: Suva-HO:-88F WGA

<400> SEQUENCE: 23
ctcttagccc tttcttcttt cc    22

<210> SEQ ID NO 24
<211> LENGTH: 22
<212> TYPE: DNA
<213> ORGANISM: Artificial Sequence
<220> FEATURE:
<223> OTHER INFORMATION: Synthetic primer: Suva-HO::+1900R WGA

<400> SEQUENCE: 24
cctgcaaata ctgttctgac ag    22

<210> SEQ ID NO 25
<211> LENGTH: 20
<212> TYPE: DNA
<213> ORGANISM: Artificial Sequence

```
<220> FEATURE:
<223> OTHER INFORMATION: Synthetic primer: Smik-HO:-168F WGA

<400> SEQUENCE: 25
accgttgaag cctattgaag                                                20

<210> SEQ ID NO 26
<211> LENGTH: 21
<212> TYPE: DNA
<213> ORGANISM: Artificial Sequence
<220> FEATURE:
<223> OTHER INFORMATION: Synthetic primer: Smik-HO:+2010R WGA

<400> SEQUENCE: 26
tttaacagaa cgtagcgtag c                                              21

<210> SEQ ID NO 27
<211> LENGTH: 27
<212> TYPE: DNA
<213> ORGANISM: Artificial Sequence
<220> FEATURE:
<223> OTHER INFORMATION: Synthetic primer: Smik-HO:-62F WGA

<400> SEQUENCE: 27
taatcataaa attcaaacct gtatccc                                        27

<210> SEQ ID NO 28
<211> LENGTH: 25
<212> TYPE: DNA
<213> ORGANISM: Artificial Sequence
<220> FEATURE:
<223> OTHER INFORMATION: Synthetic primer: Smik-HO:+1838R WGA

<400> SEQUENCE: 28
gaattaaaaa tagccattat catcc                                          25

<210> SEQ ID NO 29
<211> LENGTH: 26
<212> TYPE: DNA
<213> ORGANISM: Artificial Sequence
<220> FEATURE:
<223> OTHER INFORMATION: Synthetic primer: Suva-chr5 F WGA

<400> SEQUENCE: 29
gaaaataaca aaagaagaa aatggg                                          26

<210> SEQ ID NO 30
<211> LENGTH: 27
<212> TYPE: DNA
<213> ORGANISM: Artificial Sequence
<220> FEATURE:
<223> OTHER INFORMATION: Synthetic primer: Suva-chr5 R WGA

<400> SEQUENCE: 30
gttagggata ttctagtaaa aaaatgc                                        27

<210> SEQ ID NO 31
<211> LENGTH: 57
<212> TYPE: DNA
<213> ORGANISM: Artificial Sequence
<220> FEATURE:
<223> OTHER INFORMATION: Synthetic primer: pHERP-X #2 F WGA

<400> SEQUENCE: 31
atcctctaga gtcgacttgg atggacgcaa agaagtttaa taatcatatt acatggc       57
```

<210> SEQ ID NO 32
<211> LENGTH: 40
<212> TYPE: DNA
<213> ORGANISM: Artificial Sequence
<220> FEATURE:
<223> OTHER INFORMATION: Synthetic primer: pHERP-X #2 R WGA

<400> SEQUENCE: 32
atgcctgcag gtcgacgagc tcgtttcga cactggatgg        40

<210> SEQ ID NO 33
<211> LENGTH: 90
<212> TYPE: DNA
<213> ORGANISM: Artificial Sequence
<220> FEATURE:
<223> OTHER INFORMATION: Synthetic primer: ScerRM11-1a-ADE2:I-SceI:HERP
      F WGA

<400> SEQUENCE: 33
taggtatatc attttatatt atttgctgtg caagtatatc aataaactta tatatatggga    60 taacagggta atgtcgactt ggatggacgc        90

<210> SEQ ID NO 34
<211> LENGTH: 60
<212> TYPE: DNA
<213> ORGANISM: Artificial Sequence
<220> FEATURE:
<223> OTHER INFORMATION: Synthetic primer: ScerRM11-1a-ADE2:HERP R WGA

<400> SEQUENCE: 34
agaaaaacaa gaaaaccgga caaaacaatc aagtgagctc gttttcgaca ctggatggcg    60

<210> SEQ ID NO 35
<211> LENGTH: 60
<212> TYPE: DNA
<213> ORGANISM: Artificial Sequence
<220> FEATURE:
<223> OTHER INFORMATION: Synthetic primer: Scer-RM11-1a-ADE2-_::TK-URA3
      F

<400> SEQUENCE: 35
ttatttgctg tgcaagtata tcaataaact tatataagat ctgtttagct tgccttgtcc    60

<210> SEQ ID NO 36
<211> LENGTH: 60
<212> TYPE: DNA
<213> ORGANISM: Artificial Sequence
<220> FEATURE:
<223> OTHER INFORMATION: Synthetic primer: Scer-RM11-1a-ADE2-_::TK-URA3
      R

<400> SEQUENCE: 36
aaaacaagaa aaccggacaa acaatcaag tggtaataac tgatataatt aaattgaagc    60

<210> SEQ ID NO 37
<211> LENGTH: 26
<212> TYPE: DNA
<213> ORGANISM: Artificial Sequence
<220> FEATURE:
<223> OTHER INFORMATION: Synthetic primer: Scer-RM11-1a-ADE2:-143F WGA

<400> SEQUENCE: 37
gtatgaaatt cttaaaaaag gacacc        26

<210> SEQ ID NO 38

<211> LENGTH: 24
<212> TYPE: DNA
<213> ORGANISM: Artificial Sequence
<220> FEATURE:
<223> OTHER INFORMATION: Synthetic primer: Scer-RM11-1a-ADE2:-111F WGA

<400> SEQUENCE: 38
cgttgatttc tatgtatgaa gtcc                                          24

<210> SEQ ID NO 39
<211> LENGTH: 24
<212> TYPE: DNA
<213> ORGANISM: Artificial Sequence
<220> FEATURE:
<223> OTHER INFORMATION: Synthetic primer: Scer-RM11-1a-ADE2:+1809R WGA

<400> SEQUENCE: 39
taaattggtg cgtaaaatcg ttgg                                          24

<210> SEQ ID NO 40
<211> LENGTH: 25
<212> TYPE: DNA
<213> ORGANISM: Artificial Sequence
<220> FEATURE:
<223> OTHER INFORMATION: Synthetic primer: Scer-RM11-1a-ADE2:+1844R WGA

<400> SEQUENCE: 40
aactaaatgg acaatattat ggagc                                         25

<210> SEQ ID NO 41
<211> LENGTH: 60
<212> TYPE: DNA
<213> ORGANISM: Artificial Sequence
<220> FEATURE:
<223> OTHER INFORMATION: Synthetic primer: ScerPE-2-ADE2::Suva-ADE2 F
      WGA

<400> SEQUENCE: 41
caatcaagaa aaacaagaaa accggacaaa acaatcaagt atggattcta gaactgtcgg   60

<210> SEQ ID NO 42
<211> LENGTH: 60
<212> TYPE: DNA
<213> ORGANISM: Artificial Sequence
<220> FEATURE:
<223> OTHER INFORMATION: Synthetic primer: ScerPE-2-ADE2::Suva-ADE2 R
      WGA

<400> SEQUENCE: 42
tatttgctgt gcaagtatat caataaactt atatattatt tgtttcctaa ataagcttcg   60

<210> SEQ ID NO 43
<211> LENGTH: 60
<212> TYPE: DNA
<213> ORGANISM: Artificial Sequence
<220> FEATURE:
<223> OTHER INFORMATION: Synthetic primer: RM11-1a ADE2 mPCR F WGA

<400> SEQUENCE: 43
aatcaagaaa acaagaaaa ccggacaaaa caatcaagta tggattctag aacagttggt   60

<210> SEQ ID NO 44
<211> LENGTH: 60
<212> TYPE: DNA
<213> ORGANISM: Artificial Sequence
<220> FEATURE:
<223> OTHER INFORMATION: Synthetic primer: RM11-1a ADE2 mPCR R WGA

```
<400> SEQUENCE: 44
ttatttgctg tgcaagtata tcaataaact tatatattac ttgttttcta gataagcttc        60

<210> SEQ ID NO 45
<211> LENGTH: 60
<212> TYPE: DNA
<213> ORGANISM: Artificial Sequence
<220> FEATURE:
<223> OTHER INFORMATION: Synthetic primer: ADE2 Allele Swap C>A,M F WGA

<400> SEQUENCE: 45
caatcaagaa aaacaagaaa accggacaaa acaatcaagt atggattcta gaacagtcgg        60

<210> SEQ ID NO 46
<211> LENGTH: 60
<212> TYPE: DNA
<213> ORGANISM: Artificial Sequence
<220> FEATURE:
<223> OTHER INFORMATION: Synthetic primer: ADE2 Allele Swap C>E F WGA

<400> SEQUENCE: 46
caatcaagaa aaacaagaaa accggacaaa acaatcaagt atggattcta gaactgtcgg        60

<210> SEQ ID NO 47
<211> LENGTH: 60
<212> TYPE: DNA
<213> ORGANISM: Artificial Sequence
<220> FEATURE:
<223> OTHER INFORMATION: Synthetic primer: ADE2 Allele Swap C>K,P F WGA

<400> SEQUENCE: 47
caatcaagaa aaacaagaaa accggacaaa acaatcaagt atggattcta gaacagttgg        60

<210> SEQ ID NO 48
<211> LENGTH: 60
<212> TYPE: DNA
<213> ORGANISM: Artificial Sequence
<220> FEATURE:
<223> OTHER INFORMATION: Synthetic primer: ADE2 Allele Swap C>A R WGA

<400> SEQUENCE: 48
atattatttg ctgtgcaagt atatcaataa acttatatac tatttgtttt ctaaataagc        60

<210> SEQ ID NO 49
<211> LENGTH: 60
<212> TYPE: DNA
<213> ORGANISM: Artificial Sequence
<220> FEATURE:
<223> OTHER INFORMATION: Synthetic primer: ADE2 Allele Swap C>E R WGA

<400> SEQUENCE: 49
atattatttg ctgtgcaagt atatcaataa acttatatat tatttgtttc ctaaataagc        60

<210> SEQ ID NO 50
<211> LENGTH: 60
<212> TYPE: DNA
<213> ORGANISM: Artificial Sequence
<220> FEATURE:
<223> OTHER INFORMATION: Synthetic primer: ADE2 Allele Swap C>K R WGA

<400> SEQUENCE: 50
atattatttg ctgtgcaagt atatcaataa acttatatat tatttgcttt ctaaataagc        60

<210> SEQ ID NO 51
```

```
<211> LENGTH: 60
<212> TYPE: DNA
<213> ORGANISM: Artificial Sequence
<220> FEATURE:
<223> OTHER INFORMATION: Synthetic primer: ADE2 Allele Swap C>M R WGA

<400> SEQUENCE: 51
atattatttg ctgtgcaagt atatcaataa acttatatac tatttgtttt ctaagtaagc      60

<210> SEQ ID NO 52
<211> LENGTH: 60
<212> TYPE: DNA
<213> ORGANISM: Artificial Sequence
<220> FEATURE:
<223> OTHER INFORMATION: Synthetic primer: ADE2 Allele Swap C>P R WGA

<400> SEQUENCE: 52
atattatttg ctgtgcaagt atatcaataa acttatatat tatttgtttt ctaaataagc      60

<210> SEQ ID NO 53
<211> LENGTH: 90
<212> TYPE: DNA
<213> ORGANISM: Artificial Sequence
<220> FEATURE:
<223> OTHER INFORMATION: Synthetic primer: Scer-S288c-ADE2-_::HERP F WGA

<400> SEQUENCE: 53
tttataatta tttgctgtac aagtatatca ataaacttat atatagggat aacagggtaa      60
tttggatgga cgcaaagaag tttaataatc                                      90

<210> SEQ ID NO 54
<211> LENGTH: 60
<212> TYPE: DNA
<213> ORGANISM: Artificial Sequence
<220> FEATURE:
<223> OTHER INFORMATION: Synthetic primer: Scer-S288c-ADE2-_::HERP R WGA

<400> SEQUENCE: 54
caagaaaaac aagaaaatcg acaaaacaa tcaagtatta agggttctcg agagctcgtt       60

<210> SEQ ID NO 55
<211> LENGTH: 60
<212> TYPE: DNA
<213> ORGANISM: Artificial Sequence
<220> FEATURE:
<223> OTHER INFORMATION: Synthetic primer: Suva-chr5:HERP1.X F WGA

<400> SEQUENCE: 55
gaaagaaaag tcagcatacc ggttttcact tctgtatata gggataacag ggtaatttgg      60

<210> SEQ ID NO 56
<211> LENGTH: 60
<212> TYPE: DNA
<213> ORGANISM: Artificial Sequence
<220> FEATURE:
<223> OTHER INFORMATION: Synthetic primer: Suva-chr5:HERP1.X R WGA

<400> SEQUENCE: 56
ttaaaaaatg taggtaggtg agtaggtagg tcaaaagaaa ttaagggttc tcgagagctc      60

<210> SEQ ID NO 57
<211> LENGTH: 60
<212> TYPE: DNA
<213> ORGANISM: Artificial Sequence
<220> FEATURE:
<223> OTHER INFORMATION: Synthetic primer: Suva-chr5:yEGFP F WGA
```

```
<400> SEQUENCE: 57
aagaaaagtc agcataccgg ttttcacttc tgtatagttc gagtttatca ttatcaatac    60

<210> SEQ ID NO 58
<211> LENGTH: 60
<212> TYPE: DNA
<213> ORGANISM: Artificial Sequence
<220> FEATURE:
<223> OTHER INFORMATION: Synthetic primer: Suva-chr5:yEGFP R WGA

<400> SEQUENCE: 58
ttaaaaaatg taggtaggtg agtaggtagg tcaaagaag agtgtaaact gcgaagcttg     60

<210> SEQ ID NO 59
<211> LENGTH: 24
<212> TYPE: DNA
<213> ORGANISM: Artificial Sequence
<220> FEATURE:
<223> OTHER INFORMATION: Synthetic primer: Suva-chr5 F Seq WGA

<400> SEQUENCE: 59
acaagaaaga aaagtcagca tacc                                           24

<210> SEQ ID NO 60
<211> LENGTH: 30
<212> TYPE: DNA
<213> ORGANISM: Artificial Sequence
<220> FEATURE:
<223> OTHER INFORMATION: Synthetic primer: Suva-chr5 R Seq WGA

<400> SEQUENCE: 60
tagataataa tataataatt tcaacggagg                                     30

<210> SEQ ID NO 61
<211> LENGTH: 21
<212> TYPE: DNA
<213> ORGANISM: Artificial Sequence
<220> FEATURE:
<223> OTHER INFORMATION: Synthetic primer: S. kud. HO 1

<400> SEQUENCE: 61
tttgctttcg gtgtacattt g                                              21

<210> SEQ ID NO 62
<211> LENGTH: 20
<212> TYPE: DNA
<213> ORGANISM: Artificial Sequence
<220> FEATURE:
<223> OTHER INFORMATION: Synthetic primer: S. kud. HO 2

<400> SEQUENCE: 62
gtcagctgca ctgcgtttta                                                20

<210> SEQ ID NO 63
<211> LENGTH: 20
<212> TYPE: DNA
<213> ORGANISM: Artificial Sequence
<220> FEATURE:
<223> OTHER INFORMATION: Synthetic primer: S. kud. HO 3

<400> SEQUENCE: 63
cacgacatca atggcgtaaa                                                20

<210> SEQ ID NO 64
```

```
<211> LENGTH: 21
<212> TYPE: DNA
<213> ORGANISM: Artificial Sequence
<220> FEATURE:
<223> OTHER INFORMATION: Synthetic primer: S. kud. HO 4

<400> SEQUENCE: 64
tattcaggta aagccgcaga a                                              21

<210> SEQ ID NO 65
<211> LENGTH: 4462
<212> TYPE: DNA
<213> ORGANISM: Artificial Sequence
<220> FEATURE:
<223> OTHER INFORMATION: Synthetic: pHWA01 general cloning vector

<400> SEQUENCE: 65
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cagatctgtt tagcttgcct     420
tgtccccgcc gggtcacccg ccagcgacat ggaggcccca gaatacctca cttgacagtc     480
ttgacgtgcg cagctcaggg gcatgatgtg actgtcgccc gtacatttag cccatacatc     540
cccatgtata atcatttgca tccatacatt ttgatggccg cacggcgcga agcaaaaatt     600
acggctcctc gctgcagacc tgcgagcagg gaaacgctcc cctcacagac gcgttgaatt     660
gtccccacgc cgcgcccctg tagagaaata taaaaggtta ggatttgcca ctgaggttct     720
tctttcatat acttccttt aaaatcttgc taggatacag ttctcacatc acatccgaac     780
ataaacaacc atggcttcgt accccctgcca tcaacacgcg tctgcgttcg accaggctgc     840
gcgttctcgc ggccatagca accgacgtac ggcgttgcgc cctcgccggc agcaagaagc     900
cacggaagtc cgcctggagc ggaaaatgcc cacgctactg cgggtttata tagacggtcc     960
tcacgggatg gggaaaacca ccaccacgca actgctggtg gccctgggtt cgcgcgacga    1020
tatcgtctac gtacccgagc cgatgactta ctggcaggtg ctgggggctt ccgagacaat    1080
cgcgaacatc tacaccacac aacaccgcct cgaccagggt gagatatcgg ccggggacgc    1140
ggcggtggta atgacaagcg cccagataac aatgggcatg ccttatgccg tgaccgacgc    1200
cgttctggct cctcatgtcg gggggaggc tgggagttca catgcccgc ccccggccct     1260 caccctcatc ttcgaccgcc atcccatcgc cgcctcctg tgctaccgg ccgcgcgata      1320 ccttatgggc agcatgaccc ccaggccgt gctggcgttc gtggccctca tcccgccgac     1380
cttgcccggc acaaacatcg tgttggggc ccttccggag acagacaca tcgaccgcct      1440 ggccaaacgc cagcgccccg gcgagcggct tgacctggct atgctggccg cgattcgccg    1500
cgtttacggg ctgcttgcca atacggtgcg gtatctgcag ggcggcgggt cgtggtggga    1560
ggattgggga cagctttcgg ggacggccgt gccgccccag ggtgccgagc cccagggcaa    1620
cgcgggccca cgaccccata tcggggacac gttattacc ctgtttcggg ccccgagtt      1680 gctggcccc aacggcgacc tgtataacgt gtttgcctgg gccttggacg tcttggccaa     1740
acgcctccgt cccatgcacg tctttatcct ggattacgac caatcgcccg ccggctgccg    1800
```

```
ggacgccctg ctgcaactta cctccgggat ggtccagacc cacgtcacca ccccaggctc   1860
cataccgacg atctgcgacc tggcgcgcac gtttgcccgg gagatggggg aggctaactg   1920
atcagtactg acaataaaaa gattcttgtt ttcaagaact tgtcatttgt atagttttt    1980 tatattgtag ttgttctatt ttaatcaaat gttagcgtga tttatatttt ttttcgcctc   2040
gacatcatct gcccagatgc gaagttaagt gcgcagaaag taatatcatg cgtcaatcgt   2100
atgtgaatgc tggtcgctat actgctgtcg attcgatact aacgccgcca tccagtgtcg   2160
aaaacgagct cgaattcgag ctcggtaccc ggggatcctc tagagtcgac ctgcaggcat   2220
gcaagcttgg cgtaatcatg gtcatagctg tttcctgtgt gaaattgtta tccgctcaca   2280
attccacaca acatacgagc cggaagcata aagtgtaaag cctggggtgc ctaatgagtg   2340
agctaactca cattaattgc gttgcgctca ctgcccgctt tccagtcggg aaacctgtcg   2400
tgccagctgc attaatgaat cggccaacgc gcggggagag gcggtttgcg tattgggcgc   2460
tcttccgctt cctcgctcac tgactcgctg cgctcggtcg ttcggctgcg gcgagcggta   2520
tcagctcact caaaggcggt aatacggtta tccacagaat caggggataa cgcaggaaag   2580
aacatgtgag caaaaggcca gcaaaaggcc aggaaccgta aaaaggccgc gttgctggcg   2640 ttttccata ggctccgccc ccctgacgag catcacaaaa atcgacgctc aagtcagagg    2700
tggcgaaacc cgacaggact ataaagatac caggcgtttc ccctggaag ctccctcgtg     2760 cgctctcctg ttccgaccct gccgcttacc ggatacctgt ccgcctttct cccttcggga   2820
agcgtggcgc tttctcatag ctcacgctgt aggtatctca gttcggtgta ggtcgttcgc   2880
tccaagctgg gctgtgtgca cgaaccccc gttcagcccg accgctgcgc cttatccggt     2940
aactatcgtc ttgagtccaa cccggtaaga cacgacttat cgccactggc agcagccact   3000
ggtaacagga ttagcagagc gaggtatgta ggcggtgcta cagagttctt gaagtggtgg   3060
cctaactacg gctacactag aagaacagta tttggtatct gcgctctgct gaagccagtt   3120
accttcggaa aaagagttgg tagctcttga tccggcaaac aaaccaccgc tggtagcggt   3180 ggttttttg tttgcaagca gcagattacg cgcagaaaaa aaggatctca agaagatcct     3240
ttgatctttt ctacggggtc tgacgctcag tggaacgaaa actcacgtta agggattttg   3300
gtcatgagat tatcaaaaag gatcttcacc tagatccttt taaattaaaa atgaagtttt   3360
aaatcaatct aaagtatata tgagtaaact tggtctgaca gttaccaatg cttaatcagt   3420
gaggcaccta tctcagcgat ctgtctattt cgttcatcca tagttgcctg actccccgtc   3480
gtgtagataa ctacgatacg ggagggctta ccatctggcc ccagtgctgc aatgataccg   3540
cgagacccac gctcaccggc tccagattta tcagcaataa accagccagc cggaagggcc   3600
gagcgcagaa gtggtcctgc aactttatcc gcctccatcc agtctattaa ttgttgccgg   3660
gaagctagag taagtagttc gccagttaat agtttgcgca acgttgttgc cattgctaca   3720
ggcatcgtgg tgtcacgctc gtcgtttggt atggcttcat tcagctccgg ttcccaacga   3780
tcaaggcgag ttacatgatc ccccatgttg tgcaaaaaag cggttagctc cttcggtcct   3840
ccgatcgttg tcagaagtaa gttggccgca gtgttatcac tcatggttat ggcagcactg   3900
cataattctc ttactgtcat gccatccgta agatgctttt ctgtgactgg tgagtactca   3960
accaagtcat tctgagaata gtgtatgcgg cgaccgagtt gctcttgccc ggcgtcaata   4020
cgggataata ccgcgccaca tagcagaact ttaaaagtgc tcatcattgg aaaacgttct   4080
tcggggcgaa aactctcaag gatcttaccg ctgttgagat ccagttcgat gtaacccact   4140
```

```
cgtgcaccca actgatcttc agcatctttt actttcacca gcgtttctgg gtgagcaaaa    4200
acaggaaggc aaaatgccgc aaaaaaggga ataagggcga cacggaaatg ttgaatactc    4260
atactcttcc ttttcaata ttattgaagc atttatcagg gttattgtct catgagcgga    4320
tacatatttg aatgtattta gaaaaataaa caatagggg ttccgcgcac atttccccga    4380
aaagtgccac ctgacgtcta agaaaccatt attatcatga cattaaccta taaaaatagg    4440
cgtatcacga ggccctttcg tc                                             4462

<210> SEQ ID NO 66
<211> LENGTH: 5836
<212> TYPE: DNA
<213> ORGANISM: Artificial Sequence
<220> FEATURE:
<223> OTHER INFORMATION: Synthetic: pHERP1.0 general cloning vector

<400> SEQUENCE: 66
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctctagagt cgacttggat ggacgcaaag aagtttaata atcatattac atggcattac     480
caccatatac atatccatat acatatccat atctaatctt acttatatgt tgtggaaatg     540
taaagagccc cattatctta gcctaaaaaa accttctctt tggaactttc agtaatacgc     600
ttaactgctc attgctatat tgaagtacgg attagaagcc gccgagcggg tgacagccct     660
ccgaaggaag actctcctcc gtgcgtcctc gtcttcaccg gtcgcgttcc tgaaacgcag     720
atgtgcctcg cgccgcactg ctccgaacaa taaagattct acaatactag cttttatggt     780
tatgaagagg aaaaattggc agtaacctgg ccccacaaac cttcaaatga acgaatcaaa     840
ttaacaacca taggatgata atgcgattag ttttttagcc ttatttctgg ggtaattaat     900
cagcgaagcg atgatttttg atctattaac agatatataa atgcaaaaac tgcataacca     960
ctttaactga tactttcaac attttcggtt tgtattactt cttattcaaa tgtaataaaa    1020
gtatcaacaa aaaattgtta atatacctct atactttaac gtcaaggaga aaaaccccg    1080 gatccatgca tatgaaaaac atcaaaaaaa accaggtaat gaacctgggt ccgaactcta    1140
aactgctgaa agaatacaaa tcccagctga tcgaactgaa catcgaacag ttcgaagcag    1200
gtatcggtct gatcctgggt gatgcttaca tccgttctcg tgatgaaggt aaaacctact    1260
gtatgcagtt cgagtggaaa acaaagcat acatggacca cgtatgtctg ctgtacgatc    1320
agtgggtact gtccccgccg cacaaaaaag aacgtgttaa ccacctgggt aacctggtaa    1380
tcacctgggg cgcccagact ttcaaacacc aagctttcaa caaactggct aacctgttca    1440
tcgttaacaa caaaaaaacc atcccgaaca acctggttga aaactacctg accccgatgt    1500
ctctggcata ctggttcatg gatgatggtg gtaaatggga ttacaacaaa aactctacca    1560
acaaatcgat cgtactgaac acccagtctt tcactttcga agaagtagaa tacctggtta    1620
agggtctgcg taacaaattc caactgaact gttacgtaaa aatcaacaaa acaaaccga    1680 tcatctacat cgattctatg tcttacctga tcttctacaa cctgatcaaa ccgtacctga    1740
```

```
tcccgcagat gatgtacaaa ctgccgaaca ctatctcctc cgaaactttc ctgaaataat    1800
aggtctagag atctgtttag cttgcctygt ccccgccggg tcacccggcc agcgacatgg    1860
aggcccagaa taccctcctt gacagtcttg acgtgcgcag ctcaggggca tgatgtgact    1920
gtcgcccgta catttagccc atacatcccc atgtataatc atttgcatcc atacattttg    1980
atggccgcac ggcgcgaagc aaaaattacg gctcctcgct gcagacctgc gagcagggaa    2040
acgctcccct cacagacgcg ttgaattgtc cccacgccgc gccctgtag agaaatataa    2100 aaggttagga tttgccactg aggttcttct ttcatatact tccttttaaa atcttgctag    2160
gatacagttc tcacatcaca tccgaacata aacaaccatg gcttcgtacc cctgccatca    2220
acacgcgtct gcgttcgacc aggctgcgcg ttctcgcggc catagcaacc gacgtacggc    2280
gttgtgccct cgccggcagc aagaagccac ggaagtccgc ctggagcgga aaatgcccac    2340
gctactgcgg gtttatatag acggtcctca cgggatgggg aaaaccacca ccacgcaact    2400
gctggtggcc ctgggttcgc gcgacgatat cgtctacgta cccgagccga tgacttactg    2460
gcaggtgctg ggggcttccg agacaatcgc gaacatctac accacacaac accgcctcga    2520
ccagggtgag atatcggccg gggacgcggc ggtggtaatg acaagcgccc agataacaat    2580
gggcatgcct tatgccgtga ccgacgccgt tctggctcct catgtcgggg gggaggctgg    2640
gagttcacat gccccgcccc cggccctcac cctcatcttc gaccgccatc ccatcgccgc    2700
cctcctgtgc tacccggccg cgcgatacct tatgggcagc atgaccccec aggccgtgct    2760 ggcgttcgtg gccctcatcc cgccgacctt gccggcaca acatcgtgt tgggggccct    2820 tccggaggac agacacatcg accgcctggc caaacgccag cgccccggcg agcggcttga    2880
cctggctatg ctggccgcga ttcgccgcgt ttacgggctg cttgccaata cggtgcggta    2940
tctgcagggc ggcgggtcgt ggtgggagga ttggggacag ctttcgggga cggccgtgcc    3000
gccccagggt gccgagcccc agagcaacgc ggggcccacga ccccatatcg gggacacgtt    3060
atttaccctg tttcgggccc ccgagttgct ggcccccaac ggcgacctgt ataacgtgtt    3120
tgcctgggcc ttggacgtct tggccaaacg cctccgtccc atgcacgtct ttatcctgga    3180
ttacgaccaa tcgcccgccg gctgccggga cgccctgctg caacttacct ccgggatggt    3240
ccagacccac gtcaccaccc caggctccat accgacgatc tgcgacctgg cgcgcacgtt    3300
tgcccgggag atggggagg ctaactgatc agtactgaca ataaaaagat tcttgttttc    3360
aagaacttgt catttgtata gtttttttat attgtagttg ttctatttta atcaaatgtt    3420
agcgtgattt atattttttt tcgcctcgac atcatctgcc cagatgcgaa gttaagtgcg    3480
cagaaagtaa tatcatgcgt caatcgtatg tgaatgctgg tcgctatact gctgtcgatt    3540
cgatactaac gccgccatcc agtgtcgaaa acgagctcgt cgacctgcag gcatgcaagc    3600
ttggcgtaat catggtcata gctgtttcct gtgtgaaatt gttatccgct cacaattcca    3660
cacaacatac gagccggaag cataaagtgt aaagcctggg gtgcctaatg agtgagctaa    3720
ctcacattaa ttgcgttgcg ctcactgccc gctttccagt cgggaaacct gtcgtgccag    3780
ctgcattaat gaatcggcca acgcgcgggg agaggcggtt tgcgtattgg gcgctcttcc    3840
gcttcctcgc tcactgactc gctgcgctcg gtcgttcggc tgcggcgagc ggtatcagct    3900
cactcaaagg cggtaatacg gttatccaca gaatcagggg ataacgcagg aaagaacatg    3960
tgagcaaaag gccagcaaaa ggccaggaac cgtaaaaagg ccgcgttgct ggcgtttttc    4020
cataggctcc gcccccctga cgagcatcac aaaaatcgac gctcaagtca gaggtggcga    4080
```

```
aacccgacag gactataaag ataccaggcg tttcccctg gaagctccct cgtgcgctct    4140
cctgttccga ccctgccgct taccggatac ctgtccgcct ttctcccttc gggaagcgtg    4200
gcgctttctc atagctcacg ctgtaggtat ctcagttcgg tgtaggtcgt tcgctccaag    4260
ctgggctgtg tgcacgaacc ccccgttcag cccgaccgct gcgccttatc cggtaactat    4320
cgtcttgagt ccaacccggt aagacacgac ttatcgccac tggcagcagc cactggtaac    4380
aggattagca gagcgaggta tgtaggcggt gctacagagt tcttgaagtg gtggcctaac    4440
tacggctaca ctagaagaac agtatttggt atctgcgctc tgctgaagcc agttaccttc    4500
ggaaaaagag ttggtagctc ttgatccggc aaacaaacca ccgctggtag cggtggtttt    4560
tttgtttgca agcagcagat tacgcgcaga aaaaaggat ctcaagaaga tcctttgatc    4620
ttttctacgg ggtctgacgc tcagtggaac gaaaactcac gttaagggat tttggtcatg    4680
agattatcaa aaaggatctt cacctagatc cttttaaatt aaaaatgaag ttttaaatca    4740
atctaaagta tatatgagta aacttggtct gacagttacc aatgcttaat cagtgaggca    4800
cctatctcag cgatctgtct atttcgttca tccatagttg cctgactccc cgtcgtgtag    4860
ataactacga tacggagggc ttaccatctg gccccagtg ctgcaatgat accgcgagac    4920
ccacgctcac cggctccaga tttatcagca ataaaccagc cagccggaag ggccgagcgc    4980
agaagtggtc ctgcaacttt atccgcctcc atccagtcta ttaattgttg ccgggaagct    5040
agagtaagta gttcgccagt taatagtttg cgcaacgttg ttgccattgc tacaggcatc    5100
gtggtgtcac gctcgtcgtt tggtatggct tcattcagct ccggttccca acgatcaagg    5160
cgagttacat gatcccccat gttgtgcaaa aaagcggtta gctccttcgg tcctccgatc    5220
gttgtcagaa gtaagttggc cgcagtgtta tcactcatgg ttatggcagc actgcataat    5280
tctcttactg tcatgccatc cgtaagatgc ttttctgtga ctggtgagta ctcaaccaag    5340
tcattctgag aatagtgtat gcggcgaccg agttgctctt gcccggcgtc aatacgggat    5400
aataccgcgc cacatagcag aactttaaaa gtgctcatca ttggaaaacg ttcttcgggg    5460
cgaaaactct caaggatctt accgctgttg agatccagtt cgatgtaacc cactcgtgca    5520
cccaactgat cttcagcatc ttttactttc accagcgttt ctgggtgagc aaaaacagga    5580
aggcaaaatg ccgcaaaaaa gggaataagg gcgacacgga aatgttgaat actcatactc    5640 ttccttttc aatattattg aagcatttat cagggttatt gtctcatgag cggatacata    5700
tttgaatgta tttagaaaaa taaacaaata ggggttccgc gcacatttcc ccgaaaagtg    5760
ccacctgacg tctaagaaac cattattatc atgacattaa cctataaaaa taggcgtatc    5820
acgaggccct ttcgtc                                                    5836
```

<210> SEQ ID NO 67
<211> LENGTH: 6232
<212> TYPE: DNA
<213> ORGANISM: Artificial Sequence
<220> FEATURE:
<223> OTHER INFORMATION: Synthetic: pHERP-Gal Yeast shuttle vector
      w/URA3

<400> SEQUENCE: 67

```
tcgcgcgttt cggtgatgac ggtgaaaacc tctgacacat gcagctcccg gagacggtca     60
cagcttgtct gtaagcggat ggagctcgtt ttcgacactg gatggcggcg ttagtatcga    120
atcgacagca gtatagcgac cagcattcac atacgattga cgcatgatat tactttctgc    180
gcacttaact tcgcatctgg gcagatgatg tcgaggcgaa aaaaaatata aatcacgcta    240
```

```
acatttgatt aaaatagaac aactacaata taaaaaaact atacaaatga caagttcttg    300
aaaacaagaa tctttttatt gtcagtactg atcagttagc ctcccccatc tcccgggcaa    360
acgtgcgcgc caggtcgcag atcgtcggta tggagcctgg ggtggtgacg tgggtctgga    420
ccatcccgga ggtaagttgc agcagggcgt cccggcagcc ggcgggcgat tggtcgtaat    480
ccaggataaa gacgtgcatg ggacggaggc gtttggccaa gacgtccaag gcccaggcaa    540
acacgttata caggtcgccg ttggggggcca gcaactcggg ggcccgaaac agggtaaata    600
acgtgtcccc gatatggggt cgtgggcccg cgttgccctg gggctcggca ccctggggcg    660
gcacggccgt ccccgaaagc tgtccccaat cctcccacca cgacccgccg ccctgcagat    720
accgcaccgt attggcaagc agcccgtaaa cgcggcgaat cgcggccagc atagccaggt    780
caagccgctc gccggggcgc tggcgtttgg ccaggcggtc gatgtgtctg tcctccggaa    840
gggcccccaa cacgatgttt gtgccgggca aggtcggcgg gatgagggcc acgaacgcca    900
gcacggcctg gggggtcatg ctgcccataa ggtatcgcgc ggccgggtag cacaggaggg    960
cggcgatggg atggcggtcg aagatgaggg tgagggccgg gggcggggca tgtgaactcc   1020
cagcctcccc cccgacatga ggagccagaa cggcgtcggt cacggcataa ggcatgccca   1080
ttgttatctg ggcgcttgtc attaccaccg ccgcgtcccc ggccgatatc tcaccctggt   1140
cgaggcggtg ttgtgtggtg tagatgttcg cgattgtctc ggaagccccc agcacctgcc   1200
agtaagtcat cggctcgggt acgtagacga tatcgtcgcg cgaacccagg gccaccagca   1260
gttgcgtggt ggtggttttc cccatcccgt gaggaccgtc tatataaacc cgcagtagcg   1320
tgggcatttt ccgctccagg cggacttccg tggcttcttg ctgccggcga gggcgcaacg   1380
ccgtacgtcg gttgctatgg ccgcgagaac gcgcagcctg gtcgaacgca gacgcgtgtt   1440
gatggcaggg gtacgaagcc atggttgttt atgttcggat gtgatgtgag aactgtatcc   1500
tagcaagatt ttaaaaggaa gtatatgaaa gaagaacctc agtggcaaat cctaaccttt   1560
tatatttctc tacaggggcg cggcgtgggg acaattcaac gcgtctgtga ggggagcgtt   1620
tccctgctcg caggtctgca gcgaggagcc gtaattttg cttcgcgccg tgcggccatc    1680
aaaatgtatg gatgcaaatg attatacatg gggatgtatg ggctaaatgt acgggcgaca   1740
gtcacatcat gccccctgagc tgcgcacgtc aagactgtca aggagggtat tctgggcctc   1800
catgtcgctg gccgggtgac ccggcgggga cgaggcaagc taaacagatc tctagaccta   1860
ttatttcagg aaagtttcgg aggagatagt gttcggcagt ttgtacatca tctgcgggat   1920
caggtacggt ttgatcaggt tgtagaagat caggtaagac atagaatcga tgtagatgat   1980
cggtttgttt ttgttgattt ttacgtaaca gttcagttgg aatttgttac gcagacccct   2040
aaccaggtat tctacttctt cgaaagtgaa agactgggtg ttcagtacga tcgatttgtt   2100
ggtagagttt ttgttgtaat cccatttacc accatcatcc atgaaccagt atgccagaga   2160
catcggggtc aggtagtttt caaccaggtt gttcggatgg tttttttgt tgttaacgat    2220 gaacaggtta gccagtttgt tgaaagcttg gtgtttgaaa gtctgggcgc ccaggtgat    2280 taccaggtta cccaggtggt taacacgttc ttttttgtgc ggcggggaca gtacccactg   2340
atcgtacagc agacatacgt ggtccatgta tgctttgttt ttccactcga actgcataca   2400
gtaggtttta ccttcatcac gagaacggat gtaagcatca cccaggatca gaccgatacc   2460
tgcttcgaac tgttcgatgt tcagttcgat cagctgggat ttgtattctt tcagcagttt   2520
agagttcgga cccaggttca ttacctggtt ttttttgatg ttttttcatat gcatggatcc   2580 ggggttttt ctccttgacg ttaaagtata gaggtatatt aacaattttt tgttgatact   2640
```

```
tttattacat tgaataaga agtaatacaa accgaaaatg ttgaaagtat tagttaaagt    2700
ggttatgcag tttttgcatt tatatatctg ttaatagatc aaaaatcatc gcttcgctga    2760
ttaattaccc cagaaataag gctaaaaaac taatcgcatt atcatcctat ggttgttaat    2820
ttgattcgtt catttgaagg tttgtggggc caggttactg ccaattttc ctcttcataa    2880 ccataaaagc tagtattgta gaatctttat tgttcggagc agtgcggcgc gaggcacatc    2940
tgcgtttcag gaacgcgacc ggtgaagacg aggacgcacg gaggagagtc ttccttcgga    3000
gggctgtcac ccgctcggcg gcttctaatc cgtacttcaa tatagcaatg agcagttaag    3060
cgtattactg aaagttccaa agagaaggtt tttttaggct aagataatgg ggctcttac    3120 atttccacaa catataagta agattagata tggatatgta tatggatatg tatatggtgg    3180
taatgccatg taatatgatt attaaacttc tttgcgtcca tccaaggggg gatgtgctgc    3240
aaggcgatta agttgggtaa cgccagggtt ttcccagtca cgacgttgta aaacgacggc    3300
cagtgaattg taatacgact cactataggg cgaattggag ctccaccgcg gtggcggccg    3360
ctctagaact agtggatccc ccgggctgca ggaattcgat atcaagctta tcgataccgt    3420
cgacctcgag ggggggcccg gtacccagct ttgttccct ttagtgaggg ttaattccga    3480
gcttggcgta atcatggtca tagctgtttc ctgtgtgaaa ttgttatccg ctcacaattc    3540
cacacaacat aggagccgga agcataaagt gtaaagcctg gggtgcctaa tgagtgaggt    3600
aactcacatt aattgcgttg cgctcactgc ccgctttcca gtcgggaaac ctgtcgtgcc    3660
agctgcatta atgaatcggc caacgcgcgg ggagaggcgg tttgcgtatt gggcgctctt    3720
ccgcttcctc gctcactgac tcgctgcgct cggtcgttcg gctgcggcga gcggtatcag    3780
ctcactcaaa ggcggtaata cggttatcca cagaatcagg ggataacgca ggaaagaaca    3840
tgtgagcaaa aggccagcaa aaggccagga accgtaaaaa ggccgcgttg ctggcgtttt    3900
tccataggct cggccccct gacgagcatc acaaaaatcg acgctcaagt cagaggtggc    3960
gaaacccgac aggactataa agataccagg cgttccccc tggaagctcc ctcgtgcgct    4020
ctcctgttcc gaccctgccg cttaccggat acctgtccgc ctttctccct tcgggaagcg    4080
tggcgctttc tcaatgctca cgctgtaggt atctcagttc ggtgtaggtc gttcgctcca    4140
agctgggctg tgtgcacgaa ccccccgttc agcccgaccg ctgcgcctta tccggtaact    4200
atcgtcttga gtccaacccg gtaagacacg acttatcgcc actggcagca gccactggta    4260
acaggattag cagagcgagg tatgtaggcg gtgctacaga gttcttgaag tggtggccta    4320
actacggcta cactagaagg acagtatttg gtatctgcgc tctgctgaag ccagttacct    4380
tcggaaaaag agttggtagc tcttgatccg gcaaacaaac caccgctggt agcggtggtt    4440
tttttgtttg caagcagcag attacgcgca gaaaaaagg atctcaagaa gatcctttga    4500
tcttttctac ggggtctgac gctcagtgga acgaaaactc acgttaaggg attttggtca    4560
tgagattatc aaaaaggatc ttcacctaga tccttttaaa ttaaaaatga agttttaaat    4620
caatctaaag tatatatgag taaacttggt ctgacagtta ccaatgctta atcagtgagg    4680
cacctatctc agcgatctgt ctatttcgtt catccatagt tgcctgactg cccgtcgtgt    4740
agataactac gatacgggag ggcttaccat ctggccccag tgctgcaatg ataccgcgag    4800
acccacgctc accggctcca gatttatcag caataaacca gccagccgga agggccgagc    4860
gcagaagtgg tcctgcaact ttatccgcct ccatccagtc tattaattgt tgccgggaag    4920
ctagagtaag tagttcgcca gttaatagtt tgcgcaacgt tgttgccatt gctacaggca    4980
```

```
tcgtggtgtc acgctcgtcg tttggtatgg cttcattcag ctccggttcc caacgatcaa     5040
ggcgagttac atgatccccc atgttgtgaa aaaaagcggt tagctccttc ggtcctccga     5100
tcgttgtcag aagtaagttg gccgcagtgt tatcactcat ggttatggca gcactgcata     5160
attctcttac tgtcatgcca tccgtaagat gcttttctgt gactggtgag tactcaacca     5220
agtcattctg agaatagtgt atgcggcgac cgagttgctc ttgcccggcg tcaatacggg     5280
ataataccgc gccacatagc agaactttaa aagtgctcat cattggaaaa cgttcttcgg     5340
ggcgaaaact ctcaaggatc ttaccgctgt tgagatccag ttcgatgtaa cccactcgtg     5400
cacccaactg atcttcagca tcttttactt tcaccagcgt ttctgggtga gcaaaaacag     5460
gaaggcaaaa tgccgcaaaa aagggaataa gggcgacacg gaaatgttga atactcatac     5520
tcttcctttt tcaatattat tgaagcattt atcagggtta ttgtctcatg agcggataca     5580
tatttgaatg tatttagaaa aataaacaaa taggggttcc gcgcacattt ccccgaaaag     5640
tgccacctgg gtccttttca tcacgtgcta taaaaataat tataatttaa attttttaat     5700
ataaatatat aaattaaaaa tagaaagtaa aaaagaaat taaagaaaaa atagttttg      5760 ttttccgaag atgtaaaaga ctctaggggg atcgccaaca aatactacct tttatcttgc     5820
tcttcctgct ctcaggtatt aatgccgaat tgtttcatct tgtctgtgta gaagaccaca     5880
cacgaaaatc ctgtgatttt acattttact tatcgttaat cgaatgtata tctatttaat     5940
ctgcttttct tgtctaataa atatatatgt aaagtacgct ttttgttgaa atttttttaaa    6000 cctttgttta tttttttttc ttcattccgt aactcttcta ccttctttat ttactttcta    6060
aaatccaaat acaaaacata aaaataaata aacacagagt aaattcccaa attattccat    6120
cattaaaaga tacgaggcgc gtgtaagtta caggcaagcg atccgtccta agaaaccatt    6180
attatcatga cattaaccta taaaaatagg cgtatcacga ggccctttcg tc             6232
```

<210> SEQ ID NO 68
<211> LENGTH: 4766
<212> TYPE: DNA
<213> ORGANISM: Artificial Sequence
<220> FEATURE:
<223> OTHER INFORMATION: Synthetic: Scer-S288c-ADE2-_::HERP1.1 contains ADE2

<400> SEQUENCE: 68

```
cctcggttct gcattgagcc gccttatatg aactgtatcg aaacgttatt ttttttaatcg      60 cagacttaag caggtaatta ttccttgctt cttgttactg gatatgtatg tatgtataat     120
aagtgatctt atgtatgaaa ttcttaaaaa aggacacctg taagcgttga tttctatgta     180
tgaagtccac atttgatgta atcataacaa agcctaaaaa ataggtatat cattttataa     240
ttatttgctg tacaagtata tcaataaact tatatatagg gataacaggg taatttggat     300
ggacgcaaag aagtttaata atcatattac atggcattac caccatatac atatccatat     360
acatatccat atctaatctt acttatatgt tgtggaaatg taaagagccc cattatctta     420
gcctaaaaaa accttctctt tggaactttc agtaatacgc ttaactgctc attgctatat     480
tgaagtacgg attagaagcc gccgagcggg tgacagccct ccgaaggaag actctcctcc     540
gtgcgtcctc gtcttcaccg gtcgcgttcc tgaaacgcag atgtgcctcg cgccgcactg     600
ctccgaacaa taaagattct acaatactag cttttatggt tatgaagagg aaaaattggc     660
agtaacctgg ccccacaaac cttcaaatga acgaatcaaa ttaacaacca taggatgata     720
atgcgattag tttttttagcc ttatttctgg ggtaattaat cagcgaagcg atgatttttg     780
```

```
atctattaac agatatataa atgcaaaaac tgcataacca ctttaactga tactttcaac    840
attttcggtt tgtattactt cttattcaaa tgtaataaaa gtatcaacaa aaaattgtta    900
atatacctct atactttaac gtcaaggaga aaaaacccg gatccatgca tatgaaaaac     960
atcaaaaaaa accaggtaat gaacctgggt ccgaactcta aactgctgaa agaatacaaa   1020
tcccagctga tcgaactgaa catcgaacag ttcgaagcag gtatcggtct gatcctgggt   1080
gatgcttaca tccgttctcg tgatgaaggt aaaacctact gtatgcagtt cgagtggaaa   1140
aacaaagcat acatggacca cgtatgtctg ctgtacgatc agtgggtact gtccccgccg   1200
cacaaaaaag aacgtgttaa ccacctgggt aacctggtaa tcacctgggg cgcccagact   1260
ttcaaacacc aagctttcaa caaactggct aacctgttca tcgttaacaa caaaaaaacc   1320
atcccgaaca acctggttga aaactacctg accccgatgt ctctggcata ctggttcatg   1380
gatgatggtg gtaaatggga ttacaacaaa aactctacca acaaatcgat cgtactgaac   1440
acccagtctt tcactttcga agaagtagaa tacctggtta agggtctgcg taacaaattc   1500
caactgaact gttacgtaaa aatcaacaaa aacaaaccga tcatctacat cgattctatg   1560
tcttacctga tcttctacaa cctgatcaaa ccgtacctga tcccgcagat gatgtacaaa   1620
ctgccgaaca ctatctcctc cgaaactttc ctgaaataat aggtctagag atctgtttag   1680
cttgcctygt ccccgccggg tcaccccggcc agcgacatgg aggcccagaa tacccctcctt  1740
gacagtcttg acgtgcgcag ctcaggggca tgatgtgact gtcgcccgta catttagccc   1800
atacatcccc atgtataatc atttgcatcc atacattttg atggccgcac ggcgcgaagc   1860
aaaaattacg gctcctcgct gcagacctgc gagcagggaa acgctcccct cacagacgcg   1920
ttgaattgtc cccacgccgc gccctgtag agaaatataa aaggttagga tttgccactg   1980
aggttcttct ttcatatact ccttttaaa atcttgctag gatacagttc tcacatcaca    2040
tccgaacata aacaaccatg gcttcgtacc cctgccatca acacgcgtct gcgttcgacc   2100
aggctgcgcg ttctcgcggc catagcaacc gacgtacggc gttgcgccct cgccggcagc   2160
aagaagccac ggaagtccgc ctggagcgga aaatgcccac gctactgcgg gtttatatag   2220
acggtcctca cgggatgggg aaaaccacca ccacgcaact gctggtggcc ctgggttcgc   2280
gcgacgatat cgtctacgta cccgagccga tgacttactg gcaggtgctg ggggcttccg   2340
agacaatcgc gaacatctac accacacaac accgcctcga ccagggtgag atatcggccg   2400
gggacgcggc ggtggtaatg acaagcgccc agataacaat gggcatgcct tatgccgtga   2460
ccgacgccgt tctggctcct catgtcgggg gggaggctgg gagttcacat gccccgcccc   2520
cggccctcac cctcatcttc gaccgccatc ccatcgccgc cctcctgtgc tacccggccg   2580
cgcgatacct tatgggcagc atgacccccc aggccgtgct ggcgttcgtg gccctcatcc   2640
cgccgacctt gcccggcaca aacatcgtgt tgggggccct tccggaggac agacacatcg   2700
accgcctggc caaacgccag cgcccggcg agcggcttga cctggctatg ctggccgcga   2760
ttcgccgcgt ttacgggctg cttgccaata cggtgcggta tctgcagggc ggcggtcgt    2820
ggtgggagga ttgggacag ctttcgggga cggccgtgcc gccccagggt gccgagcccc    2880
agggcaacgc gggcccacga ccccatatcg gggacacgtt atttaccctg tttcgggccc   2940
ccgagttgct ggcccccaac ggcgacctgt ataacgtgtt tgcctgggcc ttggacgtct   3000
tggccaaacg cctccgtccc atgcacgtct ttatcctgga ttacgaccaa tcgcccgccg   3060
gctgccggga cgccctgctg caacttacct ccgggatggt ccagacccac gtcaccaccc   3120
caggctccat accgacgatc tgcgacctgg cgcgcacgtt tgcccgggag atgggggagg   3180
```

```
ctaacggagg tggaggtgga ggtggaggta tgggtaaaaa gcctgaactc accgcgacgt    3240
ctgtcgagaa gtttctgatc gaaaagttcg acagcgtctc cgacctgatg cagctctcgg    3300
agggcgaaga atctcgtgct ttcagcttcg atgtaggagg cgtggatat gtcctgcggg     3360 taaatagctg cgccgatggt ttctacaaag atcgttatgt ttatcggcac tttgcatcgg    3420
ccgcgctccc gattccggaa gtgcttgaca ttggggaatt cagcgagagc ctgacctatt    3480
gcatctcccg ccgtgcacag ggtgtcacgt tgcaagacct gcctgaaacc gaactgcccg    3540
ctgttctgca gccggtcgcg gaggccatgg atgcgatcgc tgcggccgat cttagccaga    3600
cgagcgggtt cggcccattc ggaccgcaag gaatcggtca atacactaca tggcgtgatt    3660
tcatatgcgc gattgctgat ccccatgtgt atcactggca aactgtgatg gacgacaccg    3720
tcagtgcgtc cgtcgcgcag gctctcgatg agctgatgct ttgggccgag gactgccccg    3780
aagtccggca cctcgtgcac gcggatttcg gctccaacaa tgtcctgacg gacaatggcc    3840
gcataacagc ggtcattgac tggagcgagg cgatgttcgg ggattcccaa tacgaggtcg    3900
ccaacatctt cttctggagg ccgtggttgg cttgtatgga gcagcagacg cgctacttcg    3960
agcggaggca tccggagctt gcaggatcgc cgcggctccg ggcgtatatg ctccgcattg    4020
gtcttgacca actctatcag agcttggttg acggcaattt cgatgatgca gcttgggcgc    4080
agggtcgatg cgacgcaatc gtccgatccg gagccgggac tgtcgggcgt acacaaatcg    4140
cccgcagaag cgcggccgtc tggaccgatg gctgtgtaga agtactcgcc gatagtggaa    4200
accgacgccc cagcactcgt ccgagggcaa aggaataatc agtactgaca ataaaaagat    4260
tcttgttttc aagaacttgt catttgtata gttttttttat attgtagttg ttctatttta   4320
atcaaatgtt agcgtgattt atatttttt tcgcctcgac atcatctgcc cagatgcgaa     4380
gttaagtgcg cagaaagtaa tatcatgcgt caatcgtatg tgaatgctgg tcgctatact    4440
gctgtcgatt cgatactaac gccgccatcc agtgtcgaaa acgagctcac ttgattgttt    4500
tgtccgattt tcttgttttt cttgattgtt atagtaggat gtacttagaa gagagatcca    4560
acgattttac gcaccaattt atacatgaaa tgctccataa tattgtccat ttagttctta    4620
ataaaaggtc agcaagagtc aatcacttag tattacccgg ttcgtagcca tgcaacaaga    4680
gtcatttgtc agcatagctg taataatcaa tcatgacgta agaaatgtat cataattaaa    4740
agttgttaaa gatgtcagtg ttatgt                                         4766
```

<210> SEQ ID NO 69
<211> LENGTH: 4547
<212> TYPE: DNA
<213> ORGANISM: Artificial Sequence
<220> FEATURE:
<223> OTHER INFORMATION: Synthetic: Scer-S288c-ADE2-_::HERP1.2 contains ADE2

<400> SEQUENCE: 69

```
cctcggttct gcattgagcc gccttatatg aactgtatcg aaacgttatt tttttaatcg     60
cagacttaag caggtaatta ttccttgctt cttgttactg gatatgtatg tatgtataat    120
aagtgatctt atgtatgaaa ttcttaaaaa aggacacctg taagcgttga tttctatgta    180
tgaagtccac atttgatgta atcataacaa agcctaaaaa ataggtatat cattttataa    240
ttatttgctg tacaagtata tcaataaact tatatatagg gataacaggg taatttggat    300
ggacgcaaag aagtttaata atcatattac atggcattac caccatatac atatccatat   360
acatatccat atctaatctt acttatatgt tgtggaaatg taaagagccc cattatctta    420
```

```
gcctaaaaaa accttctctt tggaactttc agtaatacgc ttaactgctc attgctatat    480
tgaagtacgg attagaagcc gccgagcggg tgacagccct ccgaaggaag actctcctcc    540
gtgcgtcctc gtcttcaccg gtcgcgttcc tgaaacgcag atgtgcctcg cgccgcactg    600
ctccgaacaa taaagattct acaatactag ctttttatggt tatgaagagg aaaaattggc    660
agtaacctgg ccccacaaac cttcaaatga acgaatcaaa ttaacaacca taggatgata    720
atgcgattag ttttttagcc ttatttctgg ggtaattaat cagcgaagcg atgattttg     780
atctattaac agatatataa atgcaaaaac tgcataacca ctttaactga tactttcaac    840
attttcggtt tgtattactt cttattcaaa tgtaataaaa gtatcaacaa aaaattgtta    900
atatacctct atactttaac gtcaaggaga aaaaccccg gatccatgca tatgaaaaac     960
atcaaaaaaa accaggtaat gaacctgggt ccgaactcta aactgctgaa agaatacaaa   1020
tcccagctga tcgaactgaa catcgaacag ttcgaagcag gtatcggtct gatcctgggt   1080
gatgcttaca tccgttctcg tgatgaaggt aaaacctact gtatgcagtt cgagtggaaa   1140
aacaaagcat acatggacca cgtatgtctg ctgtacgatc agtgggtact gtccccgccg   1200
cacaaaaaag aacgtgttaa ccacctgggt aacctggtaa tcacctgggg cgcccagact   1260
ttcaaacacc aagctttcaa caaactggct aacctgttca tcgttaacaa caaaaaaacc   1320
atcccgaaca acctggttga aaactacctg accccgatgt ctctggcata ctggttcatg   1380
gatgatggtg gtaaatggga ttacaacaaa aactctacca acaaatcgat cgtactgaac   1440
acccagtctt tcactttcga agaagtagaa tacctggtta agggtctgcg taacaaattc   1500
caactgaact gttacgtaaa aatcaacaaa acaaaccga tcatctacat cgattctatg    1560
tcttacctga tcttctacaa cctgatcaaa ccgtacctga tcccgcagat gatgtacaaa   1620
ctgccgaaca ctatctcctc cgaaactttc ctgaaataat aggtctagag atctgtttag   1680
cttgcctygt ccccgccggg tcacccggcc agcgacatgg aggcccagaa tacccctcctt  1740
gacagtcttg acgtgcgcag ctcaggggca tgatgtgact gtcgcccgta catttagccc   1800
atacatcccc atgtataatc atttgcatcc atacattttg atggccgcac ggcgcgaagc   1860
aaaaattacg gctcctcgct gcagacctgc gagcagggaa acgctcccct cacagacgcg   1920
ttgaattgtc cccacgccgc gcccctgtag agaaatataa aaggttagga tttgccactg   1980
aggttcttct ttcatatact tccttttaaa atcttgctag gatacagttc tcacatcaca   2040
tccgaacata aacaaccatg gcttcgtacc cctgccatca acacgcgtct gcgttcgacc   2100
aggctgcgcg ttctcgcggc catagcaacc gacgtacggc gttgtgccct cgccggcagc   2160
aagaagccac ggaagtccgc ctggagcgga aaatgcccac gctactgcgg gtttatatag   2220
acggtcctca cgggatgggg aaaaccacca ccacgcaact gctggtggcc ctgggttcgc   2280
gcgacgatat cgtctacgta cccgagccga tgacttactg gcaggtgctg ggggcttccg   2340
agacaatcgc gaacatctac accacacaac accgcctcga ccagggtgag atatcggccg   2400
gggacgcggc ggtggtaatg acaagcgccc agataacaat gggcatgcct tatgccgtga   2460
ccgacgccgt tctggctcct catgtcgggg gggaggctgg gagttcacat gccccgcccc   2520
cggccctcac cctcatcttc gaccgccatc ccatcgccgc cctcctgtgc tacccggccg   2580
cgcgatacct tatgggcagc atgaccccc aggccgtgct ggcgttcgtg gccctcatcc    2640
cgccgacctt gccggcaca aacatcgtgt tgggggcccc tccggaggac agacacatcg    2700
accgcctggc caaacgccag cgccccggcg agcggcttga cctggctatg ctggccgcga   2760
```

```
ttcgccgcgt ttacgggctg cttgccaata cggtgcggta tctgcagggc ggcgggtcgt    2820
ggtgggagga ttggggacag ctttcgggga cggccgtgcc gccccagggt gccgagcccc    2880
agagcaacgc gggcccacga ccccatatcg gggacacgtt atttaccctg tttcgggccc    2940
ccgagttgct ggcccccaac ggcgacctgt ataacgtgtt tgcctgggcc ttggacgtct    3000
tggccaaacg cctccgtccc atgcacgtct ttatcctgga ttacgaccaa tcgcccgccg    3060
gctgccggga cgccctgctg caacttacct ccgggatggt ccagacccac gtcaccaccc    3120
caggctccgt accgacgatc tgcgacctgg cgcgcacgtt gcccgggag atggggagg     3180 ctaacgagg tggaggtgga ggtggaggta tgggtaagga aaagactcac gtttcgaggc    3240
cgcgattaaa ttccaacatg gatgctgatt tatatgggta taaatgggct cgcgataatg    3300
tcgggcaatc aggtgcgaca atctatcgat tgtatgggaa gcccgatgcg ccagagttgt    3360
ttctgaaaca tggcaaaggt agcgttgcca atgatgttac agatgagatg gtcagactaa    3420
actggctgac ggaatttatg cctcttccga ccatcaagca ttttatccgt actcctgatg    3480
atgcatggtt actcaccact gcgatccccg gcaaaacagc attccaggta ttagaagaat    3540
atcctgattc aggtgaaaat attgttgatg cgctggcagt gttcctgcgc cggttgcatt    3600
cgattcctgt ttgtaattgt ccttttaaca gcgatcgcgt atttcgtctc gctcaggcgc    3660
aatcacgaat gaataacggt ttggttgatg cgagtgattt tgatgacgag cgtaatggct    3720
ggcctgttga acaagtctgg aaagaaatgc ataagctttt gccattctca ccggattcag    3780
tcgtcactca tggtgatttc tcacttgata accttatttt tgacgagggg aaattaatag    3840
gttgtattga tgttggacga gtcggaatcg cagaccgata ccaggatctt gccatcctat    3900
ggaactgcct cggtgagttt tctccttcat tacagaaacg ctttttcaa aaatatggta    3960 ttgataatcc tgatatgaat aaattgcagt ttcatttgat gctcgatgag ttttctaat     4020 cagtactgac aataaaaaga ttcttgtttt caagaacttg tcatttgtat agttttttta    4080
tattgtagtt gttctatttt aatcaaatgt tagcgtgatt tatatttttt ttcgcctcga    4140
catcatctgc ccagatgcga agttaagtgc gcagaaagta atatcatgcg tcaatcgtat    4200
gtgaatgctg gtcgctatac tgctgtcgat tcgatactaa cgccgccatc cagtgtcgaa    4260
aacgagctca cttgattgtt ttgtccgatt tcttgttttt tcttgattgt tatagtagga    4320
tgtacttaga agagagatcc aacgatttta cgcaccaatt tatacatgaa atgctccata    4380
atattgtcca tttagttctt aataaaaggt cagcaagagt caatcactta gtattacccg    4440
gttcgtagcc atgcaacaag agtcatttgt cagcatagct gtaataatca atcatgacgt    4500
aagaaatgta tcataattaa aagttgttaa agatgtcagt gttatgt                 4547

<210> SEQ ID NO 70
<211> LENGTH: 843
<212> TYPE: DNA
<213> ORGANISM: Herpes Simplex virus
<220> FEATURE:
<221> NAME/KEY: misc_feature
<223> OTHER INFORMATION: Thymidine kinase gene

<400> SEQUENCE: 70
atggcttcgt accccctgcca tcaacacgcg tctgcgttcg accaggctgc gcgttctcgc       60
ggccatagca accgacgtac ggcgttgcgc cctcgccggc agcaagaagc cacggaagtc      120
cgcccggagc agaaaatgcc cacgctactg cgggtttata tagacggtcc ccacgggatg      180
gggaaaacca ccaccacgca actgctggtg gccctgggtt cgcgcgacga tatcgtctac      240
```

```
gtacccgagc cgatgactta ctggcgggtg ctgggggctt ccgagacaat cgcgaacatc    300
tacaccacac aacaccgcct cgaccagggt gagatatcgg ccggggacgc ggcggtggta    360
atgacaagcg cccagataac aatgggcatg ccttatgccg tgaccgacgc cgttctggct    420
cctcatatcg gggggaggc tgggagctca catgccccgc ccccggccct caccctcatc    480
ttcgaccgcc atcccatcgc cgccctcctg tgctacccgg ccgcgcggta ccttatgggc    540
agcatgaccc ccaggccgt gctggcgttc gtggccctca tcccgccgac cttgcccggc    600
agaaacatcg tgttggggc ccttccggag gacagacaca tcgaccgcct ggccaaacgc    660
cagcgccccg tgagcggct tgacctggct atgctggccg cgattcgccg cgtttacggg    720
ctacttgcca atacggtgcg gtatctgcag tgcggcgggt cgtggcggga ggattgggga    780
cagctttcgg ggacggcctt gacgccccag ggtgccgagc cccagagcaa cgcgggccca    840
tga                                                                  843
```

<210> SEQ ID NO 71
<211> LENGTH: 280
<212> TYPE: PRT
<213> ORGANISM: Herpes Simplex virus
<220> FEATURE:
<221> NAME/KEY: misc_feature
<223> OTHER INFORMATION: Translation of TK gene

<400> SEQUENCE: 71

```
Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Arg Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
```

-continued

```
            245                 250                 255
Glu Asp Trp Gly Gln Leu Ser Gly Thr Ala Leu Thr Pro Gln Gly Ala
            260                 265                 270
Glu Pro Gln Ser Asn Ala Gly Pro
            275                 280
```